United States Patent
Fawzi et al.

[11] Patent Number: 6,036,698
[45] Date of Patent: Mar. 14, 2000

[54] EXPANDABLE RING PERCUTANEOUS TISSUE REMOVAL DEVICE

[75] Inventors: Natalie V. Fawzi, Belmont; D. Laksen Sirimanne, Palo Alto; George D. Hermann, Portola Valley; Douglas S. Sutton, Pacifica; Thomas A. Howell, Palo Alto, all of Calif.

[73] Assignee: Vivant Medical, Inc., Portola Valley, Calif.

[21] Appl. No.: 09/184,766

[22] Filed: Nov. 2, 1998

Related U.S. Application Data

[63] Continuation-in-part of application No. 09/183,590, Oct. 30, 1998.

[51] Int. Cl.[7] .................................................. A61B 17/32
[52] U.S. Cl. ............................................ 606/114; 600/562
[58] Field of Search ............................ 606/114; 600/562, 600/564, 566, 567

[56] References Cited

U.S. PATENT DOCUMENTS

| | | |
|---|---|---|
| 4,699,154 | 10/1987 | Lindgren . |
| 4,935,025 | 6/1990 | Bundy et al. . |
| 5,183,464 | 2/1993 | Dubrul et al. . |
| 5,431,676 | 7/1995 | Dubrul et al. . |
| 5,443,472 | 8/1995 | Li .......................................... 606/114 |
| 5,454,790 | 10/1995 | Dubrul et al. . |
| 5,782,840 | 7/1998 | Nakao . |
| 5,814,052 | 9/1998 | Nakao et al. ........................... 606/115 |
| 5,855,576 | 1/1999 | LeVeen et al. . |
| 5,857,981 | 1/1999 | Bucalo et al. . |
| 5,857,982 | 1/1999 | Milliman et al. . |
| 5,882,316 | 3/1999 | Chu et al. . |
| 5,904,690 | 5/1999 | Middleman et al. .................... 606/113 |

OTHER PUBLICATIONS

"Line of Minimally Invasive Biopsy Devices added to HSCA—U.S. Surgical Agreements", Hospital Materials Management, No. 7, vol. 23, Jul. 1, 1998 (no author cited).

"FDA Gives OK to USS Breast–Biopsy System", Medical Industry Today, Dec. 12, 1997 (no author cited).

Imagyn Surgical Product Literature, Siteselect Stereotactic Breast Biopsy System, (including article entitled: Breast Disease: Assessment and Management of Breast Complaints, Spring 1995 (no author cited).

*Primary Examiner*—Gene Mancene
*Assistant Examiner*—Michael B Priddy
*Attorney, Agent, or Firm*—Morrison & Foerster LLP

[57] ABSTRACT

This is a device for percutaneous tissue sampling or excision. In particular, it uses an expandable ring cutter which produces an accurately located, discrete tissue mass that is removable through a comparatively much smaller access member. The tissue mass is easily reconstructed to its original form and orientation once taken from the body for further study.

108 Claims, 14 Drawing Sheets

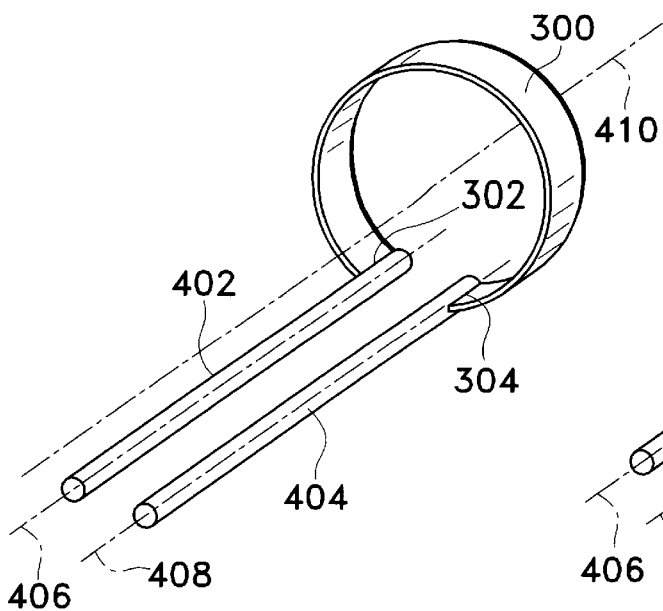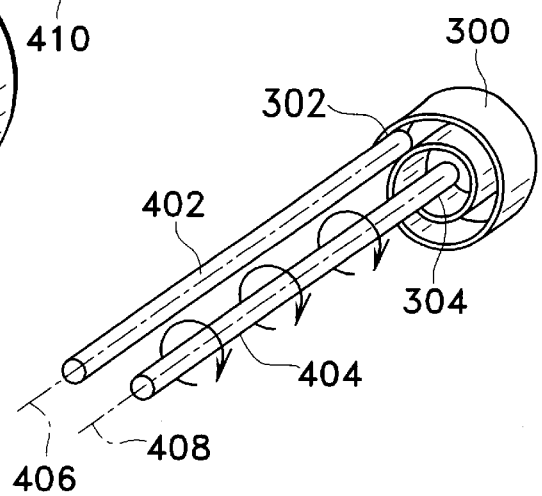
FIG. 5A    FIG. 6A
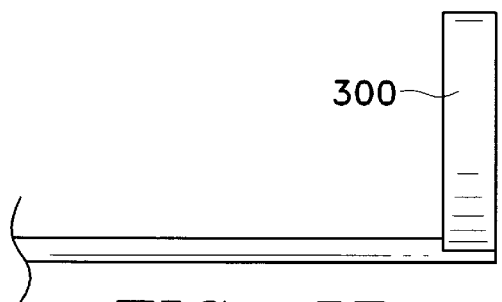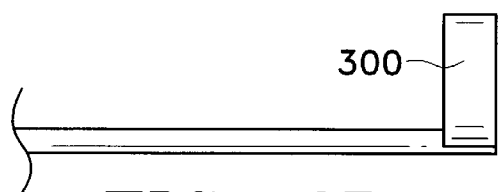
FIG. 5B    FIG. 6B
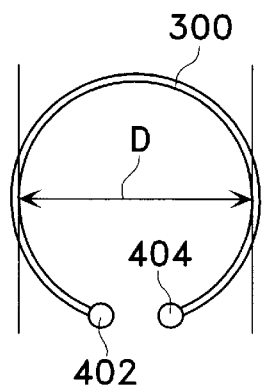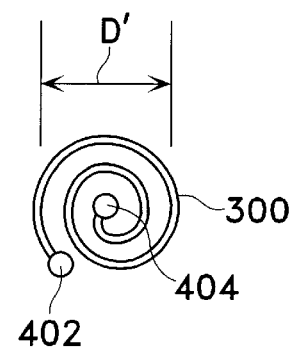
FIG. 5C    FIG. 6C

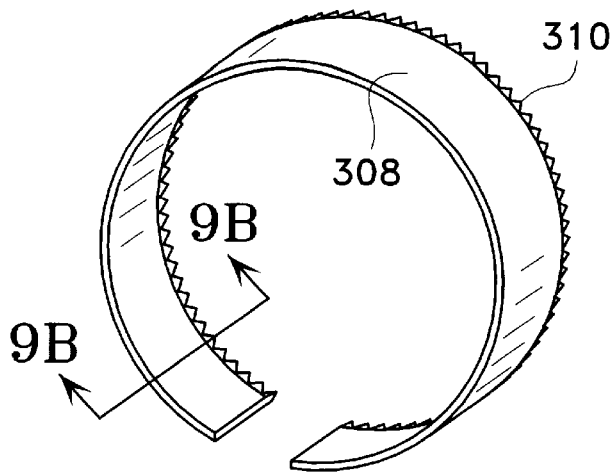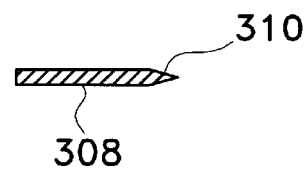
FIG. 9A  FIG. 9B
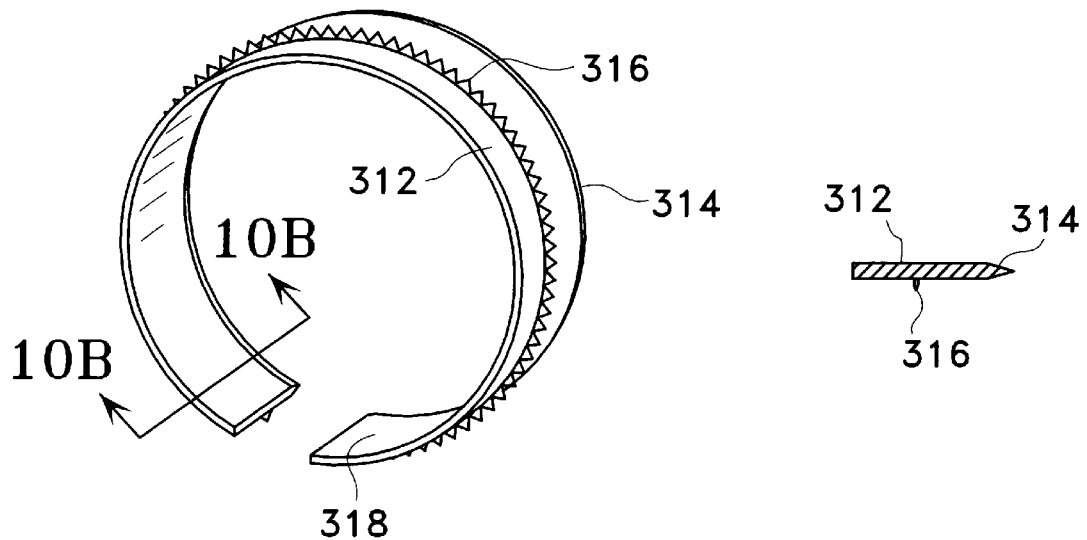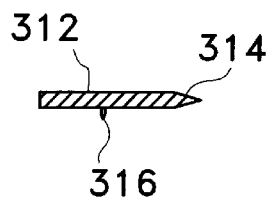
FIG. 10A  FIG. 10B

EXPANDABLE RING PERCUTANEOUS TISSUE REMOVAL DEVICE

CROSS-REFERENCE TO RELATED APPLICATION

This application is a continuation-in-part of U.S. application Ser. No. 09/183,590, filed Oct. 30, 1998, entitled EXPANDABLE RING PERCUTANEOUS TISSUE REMOVAL DEVICE, the entirety of which is hereby incorporated by notice.

FIELD OF THE INVENTION

This invention relates to a device and to a related procedure for percutaneous tissue sampling or excision. In particular, it uses an expandable ring cutter which produces an accurately located, discrete tissue mass that is removable through a comparatively much smaller tissue access device. The tissue mass maintains orientation once taken from the body for further study.

BACKGROUND OF THE INVENTION

Despite the advances made in technologies such as medical imaging to assist the physician in early stage diagnosis and treatment of patients with possible atypical tissue such as cancer, it is still often necessary to sample difficult-to-reach organ or tissue lesions by biopsy to confirm the presence or absence of abnormalities or disease.

A disease for which biopsy is a critical tool is breast cancer. This affliction is responsible for 18% of all cancer deaths in women and is the leading cause of death among women aged 40 to 55. As with many diseases and other types of cancer, early detection and diagnosis of breast cancer is critical in providing the best chance of survival.

In the majority of cases, detection of the disease is first made when a patient discovers a palpable mass through self-examination and consults her physician. For breast lesions that are more difficult or impossible to detect through palpation, diagnostic techniques such as x-ray mammography and, more recently, digital mammography, and scintamammography are invaluable. Other techniques such as ultrasound, magnetic resonance, the Dilon gamma camera, position emission tomography, MIBI, computed topography, fluoroscopy, thermography, transillumination and diaphanography can also be used to help determine the presence and nature of suspect tissue.

Of these technologies, the primary clinical diagnostic tool for the detection of breast cancer is x-ray mammography. Over 15 million mammograms are performed each year in the United States alone. Mammography uses x-rays to image breast tissue, identifying areas of high density as possible lesions.

Unfortunately, the limitations of technologies such as mammography in accurately detecting precancerous or cancerous lesions in the breast are significant. Among these limitations is the fact that only one out of every five lesions discovered through x-ray mammography proves to be cancerous. Roughly 25% of women have dense breast tissue, which is notoriously difficult to inspect via mammography. Also, mammography is generally less effective for women under 40 years of age. For younger women, therefore, self-examination for palpable lesions or ultrasound examination is important. However, neither of these techniques is able to detect microcalcifications, important possible precursors to cancer.

As long as there is a degree of uncertainty associated with these various diagnostic techniques, biopsies must be performed to sample the suspicious tissue to determine its exact nature and pathology.

In the detection and treatment of breast cancer, there are two general classes of biopsy: the minimally invasive percutaneous fine or core needle biopsy and the more invasive surgical or "open" biopsy.

Open biopsies, both incisional and excisional, are advisable when suspicious lumps should be removed in their entirety or when core needle biopsies don't give complete information about the nature of the lesion.

One this type of open biopsy is the wire localization biopsy. Such a procedure includes the following steps: first, a radiologist inserts a wire into the breast under x-ray guidance to mark the location of the suspect tissue. The tissue is then removed by a surgeon for examination by a pathologist. Although large tissue samples are removed by this technique, the risk of permanent disfigurement, the attendant morbidity and mortality risks associated with surgery, and long hospital recovery times are but three of the many disadvantages associated with open surgical biopsies.

Of the less invasive class of percutaneous biopsies, the least invasive is known as a fine needle biopsy. For palpable lumps, a physician inserts a needle and syringe directly into the lump to obtain a cell sample which is then examined by a cytologist. For non-palpable lesions identified by x-ray mammography or other diagnostic tool, fine needle biopsies are often performed under stereotactic or ultrasonic guidance. Here, multiple mammograms are taken of the breast and the images are analyzed by a computer to determine the location of the suspect lesion in three dimensions. The physician then penetrates the breast with a needle, targeting the suspect region and removing a small number of cells. There are two significant drawbacks to fine needle biopsy techniques: first, several specimens must be taken to ensure the lesion is well-sampled. Secondly, the limited size of the specimens obtained under fine needle biopsy dictate that a skilled cytologist be involved to analyze the suspect cells out of context of the surrounding healthy tissue.

A second type of percutaneous needle biopsy used to obtain a larger specimen is known as a core biopsy. With this procedure, a larger needle is inserted into the breast via an incision in the skin under stereotactic or ultrasonic guidance. A spring-loaded device is then fired into the breast to obtain a single core sample of tissue, preferably through the center of the lesion. The larger specimen size (up to 20 mm in diameter) obtained by this technique can be more accurately read by a pathologist, who can analyze the suspect cells in the context of the surrounding tissue. Examples of such devices are described in U.S. Pat. No. Re. 34,056 and U.S. Pat. Nos. 4,944,308 and 4,953,558, the entirety of which are hereby incorporated by reference.

Traditionally, as with fine needle biopsies, core biopsies require multiple core samples, typically four to twenty, to ensure an accurately representative sample of the suspect region is profiled. This means that as many as twenty separate needle insertions must be made into the breast through the skin.

More recently developed needle biopsy technologies are directed to solving this problem by allowing multiple samples to be obtained through a single incision, such as that described in U.S. Pat. Nos. 5,709,697 and 5,782,775, the entirety of which are hereby incorporated by reference. One such technology, described in U.S. Pat. Nos. 5,526,822, 5,769,086, and 5,775,333, the entirety of which are hereby incorporated by reference, utilizes a trocar-tipped probe which is positioned in the breast under stereotactic or ultrasonic guidance to align the suspect lesion with an aperture that extends along a specified length of the probe. The tissue is then aspirated into the aperture where a rotating cutter in the probe is advanced distally to cut and capture tissue specimen into the probe lumen. The cutter is then withdrawn, transporting the specimen to a tissue collection chamber. Next, the probe, which is still in the breast, is radially rotated in position through a desired angle to align the aperture with another target tissue area. The steps of rotation, cutting, and collection, which can be automated and assisted by vacuum, are repeated until the desired number of samples is obtained.

Although this type of device requires only a small, single incision to obtain a number of core samples, each sample is still limited in size, requiring excision of multiple specimens for accurate pathologic diagnosis. As with other percutaneous excisional devices in which multiple specimens must be obtained, it is often difficult to reconstruct the spatial location and orientation of the suspect tissue as it resided in the breast prior to excision, resulting in a concomitantly difficult pathological analysis.

Another type of percutaneous excisional breast biopsy device designed to first separate healthy tissue from suspect tissue prior to obtaining a single suspect tissue sample is generally described in U.S. Pat. Nos. 5,111,828, 5,197,484, and 5,353,804, the entirety of which are hereby incorporated by reference. This device, however, requires the use of a relatively large diameter cannula to obtain an adequate specimen size.

What is needed is a small-diameter percutaneous excisional biopsy device that allows a physician to obtain, in a minimally invasive manner, a relatively large tissue specimen through a small incision. Further, what is needed is a device that can obtain a specimen large enough for a complete, accurate and satisfactory pathologic determination, obviating the need for obtaining multiple core specimens and reconstructing them ex vivo.

BRIEF DESCRIPTION OF THE DRAWINGS

FIGS. 5A to 5C show perspective, side, and end views of a variation of the cutting member in an expanded configuration together with first and second access members.

FIGS. 6A to 6C show perspective, side, and end views of a variation of the cutting member in a collapsed configuration together with first and second access members.

FIGS. 9A to 9B show perspective and cross-sectional views of a ribbon cutting member, having a leading edge serrated cutting surface, in an expanded configuration.

FIGS. 10A to 10B show perspective and cross-sectional views of a ribbon cutting member, having a mid-span serrated cutting surface and a leading edge knife-edge cutting surface, in an expanded configuration.

DESCRIPTION OF THE INVENTION

As noted above, this invention relates to devices and procedures for removing integral volumes of tissue, typically breast tissue, via percutaneous access. The diameter of the tissue volume removed using this invention is larger than the diameter of the access device. Depending upon the size of the device selected, the inventive device may be used for biopsy samples or for excision of larger amounts of tissue containing "suspicious areas" or tumorous masses. Because of the method in which the device operates, the trauma caused by removal of the chosen volume is significantly lessened as compared to other available devices. This translates to minimized recovery time, little-to-no scarring, lower risk for infection and hemotoma formation, and other advantages when compared to conventional processes. Although the devices and procedures described and claimed herein are preferably utilized in the removal of suspect breast tissue, they are not so limited. These devices may also be effectively used for in number of other areas of the body, such as the liver, the prostate, lymph nodes, and the like. In general, any organ or portion of the body where minimally invasive techniques such as herein described, where a relatively large tissue specimen is obtained through a small incision, is expressly within the scope of this invention. Therefore, the claims herein should be accordingly read.

In general, the procedure involved is this: first, a target tissue mass is selected. A trocar, localization wire, tubular vessel removal member, and a cutting member are assembled and introduced percutaneously to the vicinity of the volume to be removed. The localization wire penetrates through the target tissue mass, and the trocar is withdrawn. The cutting member is positioned to excise a generally cylindrical mass of tissue. The cylinder may be removed as a single specimen after the cutting is completed or during the step of producing the cut. In addition, the tissue may be cut into smaller specimens during the procedure. The step of cutting may be variously assisted by the use of radio frequency (RF) energy, ultrasound, mechanical energy such as cutting, vibrating and rotating, or any combination thereof.

Figure 1:
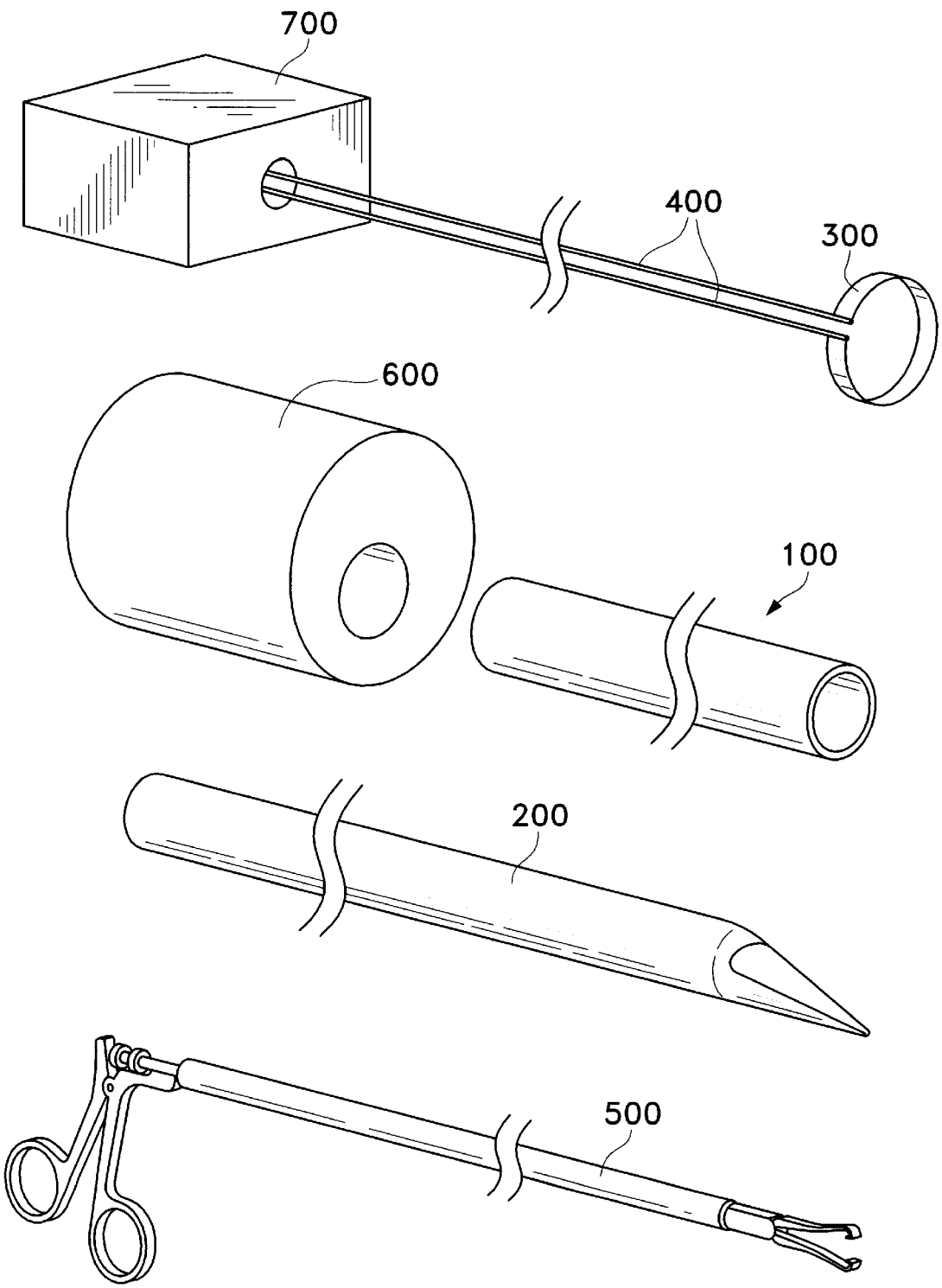
FIG. 1 shows an assemblage of the components, as in a kit, which make up the inventive tissue removal assembly.

FIG. 1 shows, in generic fashion, the components typically used in the inventive procedure. Tissue removal member (100) is shown in FIG. 1 as typically having a single lumen. This lumen is for both the removal of excised tissue from the targeted body site and for positioning the cutting member (300), as will be discussed below. The trocar (200), which fits within the larger lumen in tissue removal member (100), is also shown. Trocar (200) is used to penetrate the skin and tissue and thereby to position the distal end of the tubular tissue removal member (100) in the region of the tissue volume to be removed.

FIG. 1 shows a typical cutting member (300). Attached to cutting member (300) are two shafts (400) that typically are placed within the smaller lumen of tissue removal member (100). One shaft is typically rotationally fixed, while the other shaft is typically axially rotatable so that cutting member (300) can assume a collapsed, low-profile configuration or, upon axial rotation of one of the shafts (400), the expanded configuration as shown in FIG. 1. Cutting member (300) will generally assume a collapsed configuration (not shown) while in the lumen of tissue removal member (100). As the cutting member shafts (400) and cutting member (300) situated in the lumen of tissue removal member (100) are advanced distally out of tissue removal member (100), the rotatable shaft is rotated to expand the cutting member (300) as it advances, cutting through tissue so that a generally cylindrical or football-shaped mass of tissue is cut at the chosen site. The lesion or tumor is targeted so that it is situated within that chosen cylindrical or football-shaped region.

After cutting the distal end of the tissue specimen to excise it, the tissue is then removed from the body by any number of methods such as, for example, use of a removal member (500) such as that shown in FIG. 1. Desirably, the tissue is placed in tissue collection chamber assembly (600) for later study. Additional tissue specimens can also optionally be removed from the body site if desired. The tissue removal member (100) is then removed from the body site.

Generally, the region to be excised is identified using stereotactic, ultrasonic, or other indexing apparatus as is well known in the art. It is typical that the advancement of the cutting member (300) is controlled using a controller box (700) such as that depicted in FIG. 1.

Tissue Removal Member

Figure 2A:
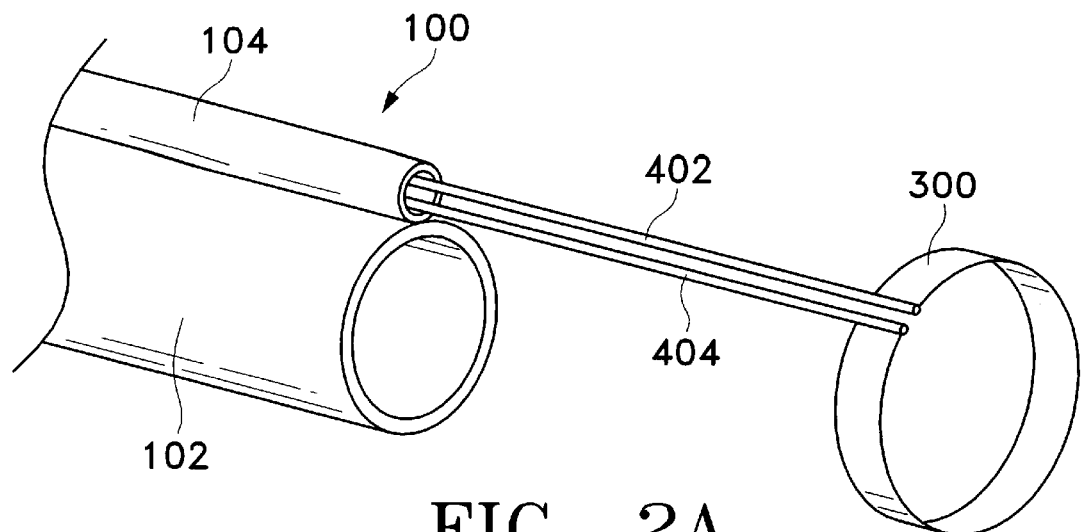
FIGS. 2A to 2J show variations of the tissue removal member and their relation to the expandable cutting member.

FIG. 2A shows a variation of the inventive tissue removal member (100). This variation includes a larger lumen member (102) and a smaller lumen member (104) which is exterior to large lumen member (102). An expandable cutting member (300) is shown attached to shafts (402) and (404) extending from small lumen member (104). Central to this invention is the concept that the cutting member (300) is capable of excising a tissue specimen which is significantly larger in diameter than is the large lumen member (102) of the tissue removal member (100). Tissue removal member (100) can be constructed from any of a large number of polymers typically used in this service, e.g., NYLON, reinforced NYLON, polypropylene, polyethyleneterephthalate (PET), polyesters, fluorocarbon plastics (e.g., TEFLON), etc. The polymers may be reinforced by fibers or filled. As will also be discussed below, the tissue removal member may be reinforced or made radially expandable using coils or braids of metals, alloys, or polymers (natural or synthetic) included in the member. The member (100) or braids may be made at least partially radio-opaque by introduction of, e.g., powdered tantalum, powdered tungsten, bismuth carbonate, and other known particulate and fibrous radio-opacifiers. Radio-opaque markers or crimps may singly or additionally be used on member (100) or the braids to serve this purpose. Tissue removal member (100) may also be partially or entirely coated and possibly cured with coating materials such as high-elongation silicone or room-temperature vulcanizing rubber or the like. Such coatings generally serve to enhance the functionality of tissue removal member (100) without sacrificing its performance characteristics, such as radial expandability.

Figure 2B:
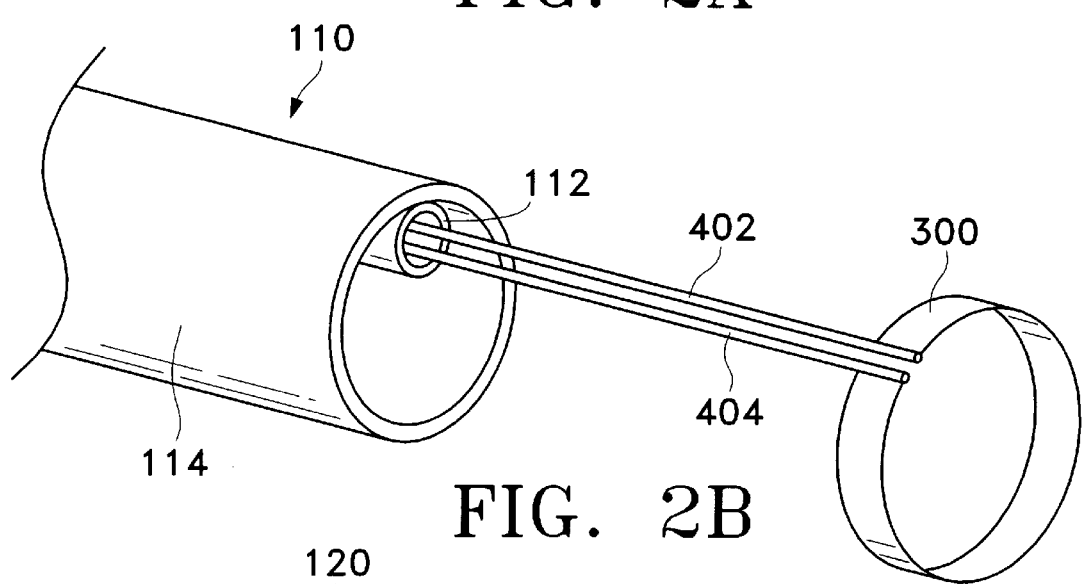

FIG. 2B shows a similar tissue removal member (110). In this variation, the small lumen tubular portion (112) is not exterior to but is instead within the large lumen member (114). Again, the cutting member (300) is shown attached to two shafts (402), (404) extending from the small lumen tubular member (112).

Figure 2C:
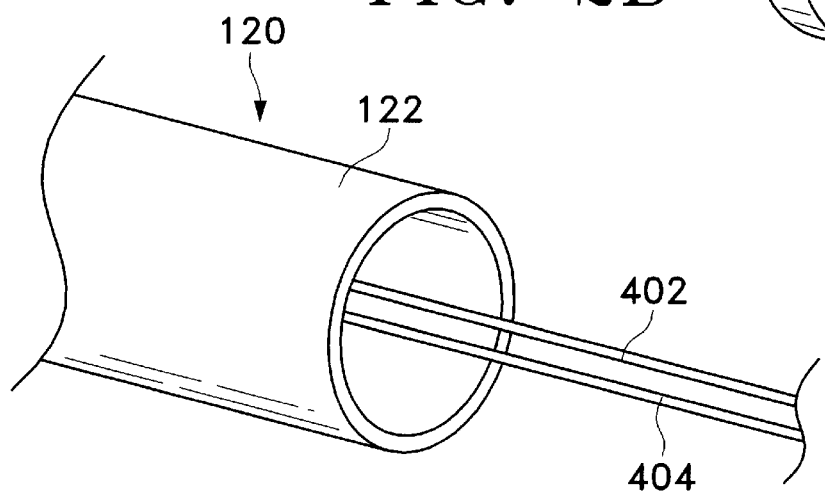

FIG. 2C shows a more typical variation in which the cutting member (not shown) and its two attendant shafts (402), (404) are disposed in the tissue removal member (120) having only a single lumen member (122). This simple variation is less complex and more suitable for use when the tissue removal member (120) is elastically expandable as described below.

Figure 2D:
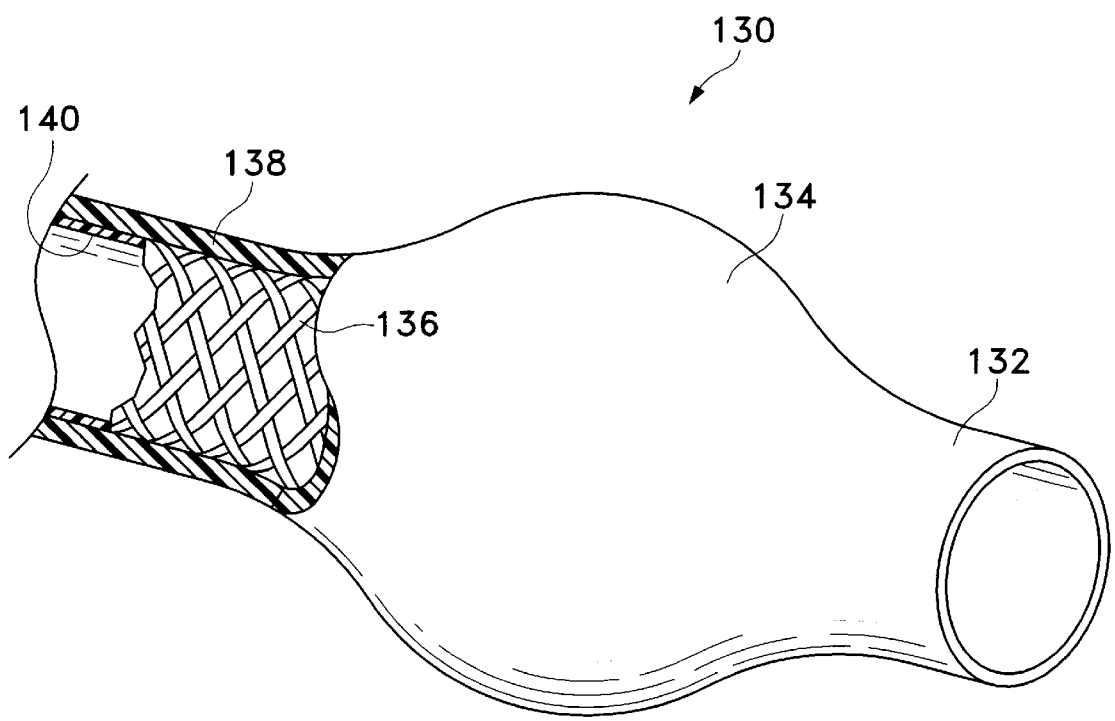

FIG. 2D is a partial cutaway of another variation of the tissue removal member (130). In this variation, the tubular portion (132) of the removal member is elastically expandable. This is depicted by the expanded portion (134) shown in FIG. 2D. An expandable outer tubular section is suitable with any of the variations described above. This variation, however, is expandable due to the use of a woven braid (136) and an elastomeric polymer forming the outer layer (138) of the device. An optional inner layer (140) is also depicted in FIG. 2D but an such inner layer (140) is not, obviously, absolutely necessary. It is convenient and desirable, however.

Figure 2E:
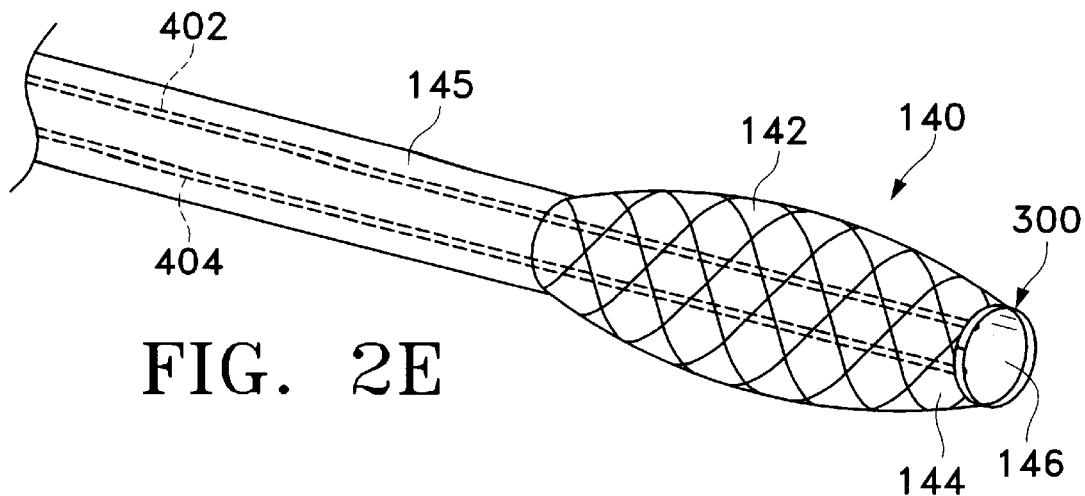

FIG. 2E is yet another variation of the tissue removal member (140). In this variation, the tubular portion (142) is elastically expandable in the same way as described above. The distal end (144) of tubular portion (142) is, however, attached to cutting member (300), and member (140) is partially covered by sheath (145) as will be described later. Tubular tissue removal member (140) may be attached to cutting member (300) by any conventional means. For instance, they may be joined mechanically or joined integrally from identical, similar, or dissimilar materials, such as metal or plastic. Further, an additional joining member (not shown) may serve to join tubular member (140) to cutting member (300). It is important, regardless of the joining means or method, that cutting member (300) be allowed to expand and contract with rotation of one of the shafts (402) and (404) as will be described in detail later. This embodiment is characterized by the fact that expansion and contraction of cutting member (300) will concomitantly expand and contract the distal end (144) of the tubular tissue removal member (140). In this way, as a tissue specimen is cut by cutting member (300), forward advancement of the cutting member (300) will allow the tissue removal member distal end (144) to assimilate a tissue specimen as tubular portion (142) expands to accommodate the tissue specimen as it is excised. Such a design enables the device to be fully operable without the use of a removal member (500) (not shown), as the entire device may be pulled from the body once the tissue specimen is inside lumen (146) of tubular portion (142). This does not mean, however, that the embodiment of FIG. 2E cannot be used with a removal member (500); for instance, such a removal member can be used to assist removing tissue through the proximal end of tissue removal member or when multiple tissue specimens are to be removed without having to remove the entire assembly from the body.

Figure 2F:
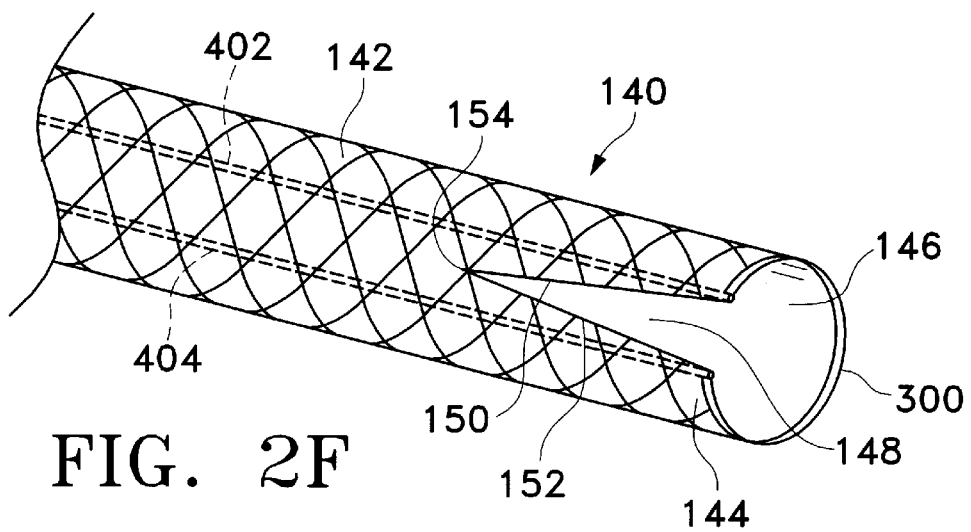

FIG. 2F depicts another variation. Here, the first and second access members, or shafts, (402) and (404), are attached to the tubular tissue removal member (140) in the general proximity of the removal member distal end (144).

Figure 2G:
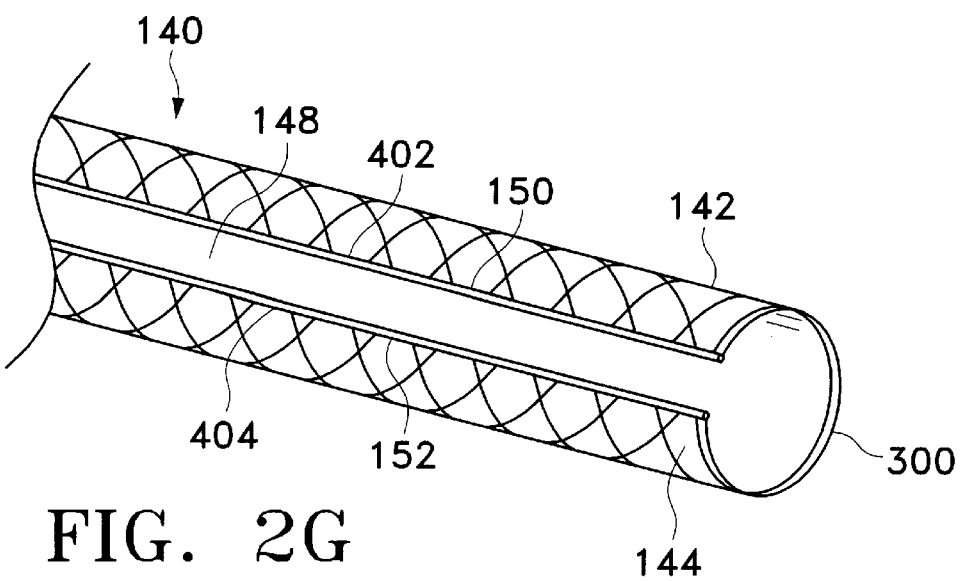

The distal end (144) of member (140) can be split in a direction parallel to the longitudinal axis of member (140), creating a longitudinal aperture (148), or gap, and two attendant edges (150) and (152) in tissue removal member (140). This aperture (148) may extend partially down the length of member (140) as shown in FIG. 2F, or completely, as shown in FIG. 2G. In either case, shafts (402) and (404) may be attached, temporarily or permanently, to tissue removal member (140) in the vicinity of edges (150) and (152). In the case where aperture (148) is partial, as shown in FIG. 2F, shafts (402) and (404) will align with edges (150) and (152) at the distal end (144) of tissue removal member (140), and run generally parallel to edges (150) and (152), diverging slightly as edges (150) and (152) merge at vertex (154).

In the embodiment of FIG. 2G, where the gap (148) exists the entire length of tissue removal member (140), the shafts (402) and (404) can be connected at edges (150) and (152) or at least substantially parallel to the edges. However, it is within the scope of the invention that shafts (402) and (404) need not be so configured with respect to edges (150) and (152) for the device to work properly.

As will be described in greater detail, one of the shafts (402), or access members, is preferably rotatably fixed. Likewise, the other shaft (404) is preferably axially rotatable so that it may expand and collapse cutting member (300), and in the case of the FIGS. 2E–2G embodiments, some or all of tissue removal member (140). The entire device may also be axially rotatable about the tissue removal member (140) longitudinal axis (not shown).

In the FIG. 2F embodiment, the aperture (148) acts to facilitate collapse of cutting member (300) in that rotation of shaft (404) will also collapse tissue removal member (140) so that the aperture (148) reduces in size as edges (150) and (152) move closer, meet, or even substantially overlap along all or a portion of their length. Expansion of cutting member (300) and tissue removal member (140) by axial rotation of access member (404) in the opposite direction, as explained in detail later, will likewise act to expand member (140), widen aperture (148), and move edges (150) and (152) further apart.

Figure 2H:
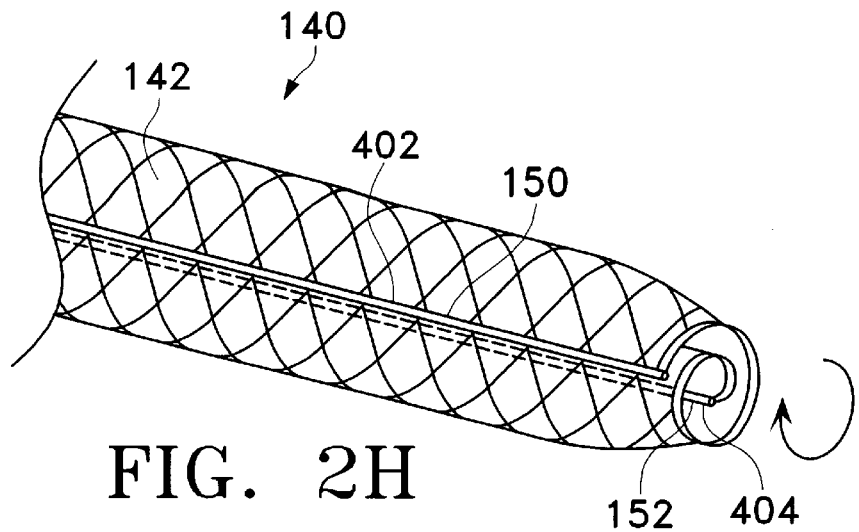
Figure 2I:
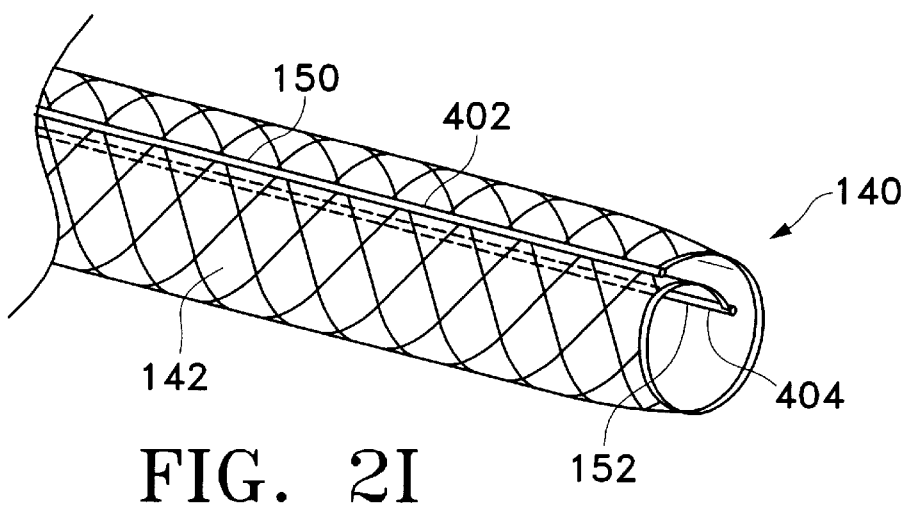

When gap (148) takes on the form shown in FIG. 2G, rotation of shaft (404) will uniformly cause tissue removal member to collapse in a manner similar or identical to cutting member (300), such that edges (150) and (152) close aperture (148) by moving together as edge (152) collapses in-on itself (FIG. 2H) or, alternatively or in conjunction with the movement described immediately above, the entire edge (152) is translated to close aperture (148) and move edge (152) closer to, or overlap, edge (150) (FIG. 2I). This complex movement of edges (150) and (152) by axial rotation of access member (404), translation of access member (404) with edge (152), singly and in combination with one another or with rotation and translation of the entire assembly, in conjunction with cutting member (300), provides a wide variety of configurations and tissue excision capabilities, the entirety of which are within the scope of this invention.

Shafts (402) and (404) may be fixed, temporarily, removably or permanently to tissue removal member (140) in a wide variety of configurations, such as in the lumen (146) side of member (140), on the exterior side of member (140), and within the structure of member (140) as described, for instance, in conjunction with FIG. 2D. As long as shaft (404) is rotatable as herein described, and shaft (402) is fixed as herein described any attachment configuration is acceptable.

Figure 2J:
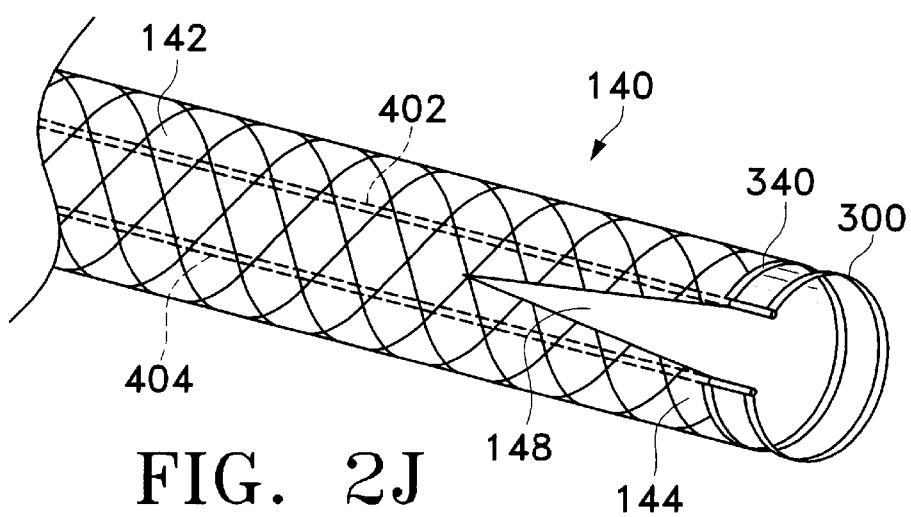

FIG. 2J shows a dual-ring configuration in which an aperture (148) exists as described above. A second ring (340) is fixed to the distal end (144) of tubular tissue removal member (140) as described above for the cutting ring (300); however, ring (340) is not for excising tissue. This second ring (340) provides a removable attachment site for cutting member (300) so that tubular portion (142) may expand and contract with cutting member (300) as described herein. Second ring (340) may have its own shafts (not shown) or may be attached to shafts (402) and (404) of ring (300). Ring (340), when used with radio frequency cutting, may be insulated with any acceptable means, such as a coating, or inherently by virtue of its composition, to insulate tissue removal member (140) from RF energy. Aperture (148) can be partial (shown) or full (not shown).

The embodiment of FIGS. 2A–2J may be used with radio frequency cutting, mechanical cutting, ultrasound cutting, or any combination thereof. The relatively large aperture (148) shown in FIGS. 2F, 2G and 2J is obviously exaggerated for purposes of clarification.

Tissue Collection Chamber Assembly

Figure 3:
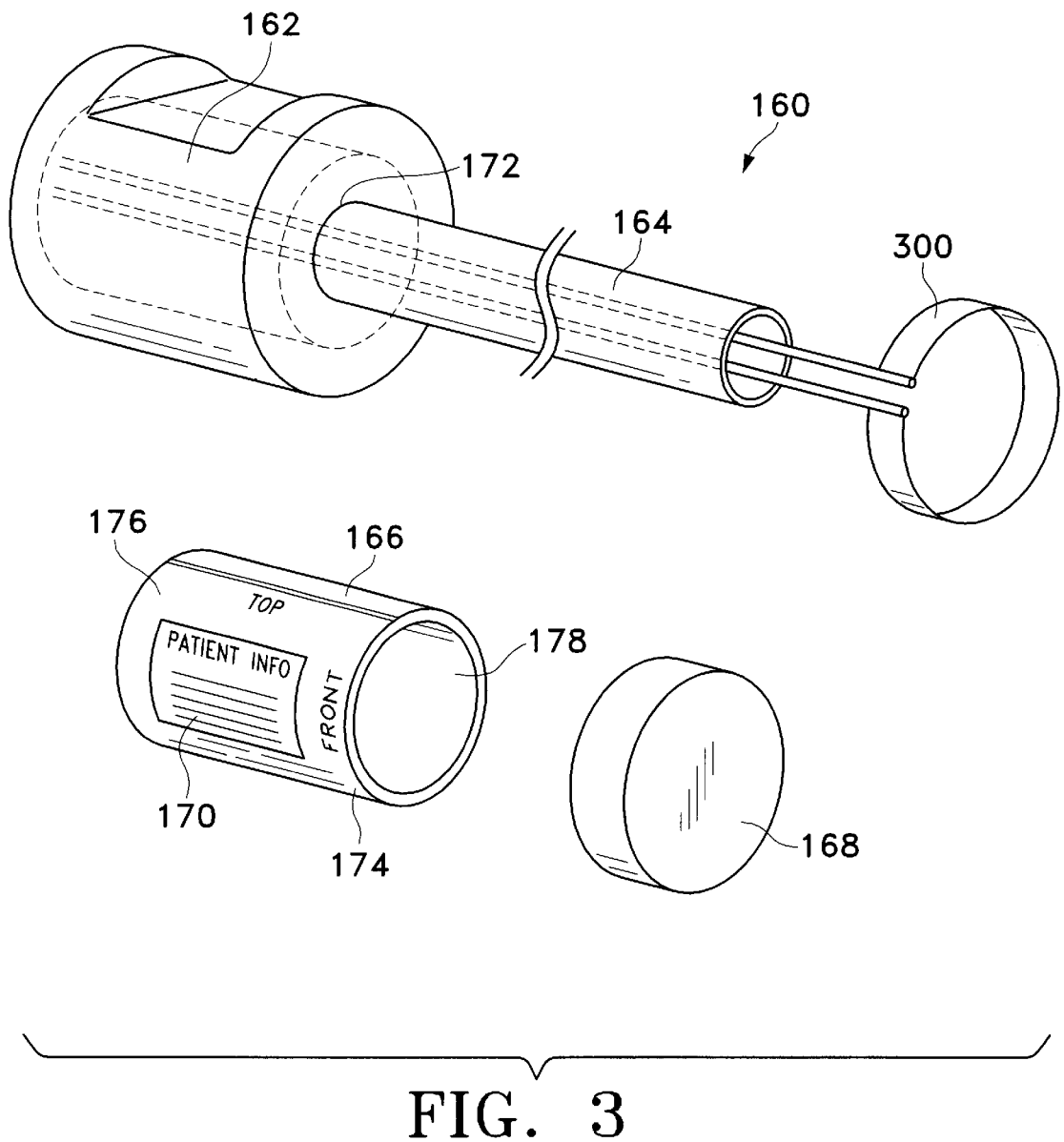
FIG. 3 shows another variation of the tissue removal member, its associated cutting member, and a desirable manner for transporting the accumulated tissue for later analysis.

FIG. 3 shows another variation of the inventive tubular tissue removal member (160). Of particular instance in this variation is the presence of a receiver, or tissue collection chamber assembly (162) situated at the proximal end of the tubular tissue removal member assembly (164).

Of special interest is the tissue collection chamber, or specimen collector (166) which may be fitted within tissue collection chamber assembly (162). The position of the tissue cutting member (300) can be indexed with the position of the tissue collector (166) so that as the tissue is removed through the tubular tissue removal member (164), it ultimately resides in the tissue collection chamber (166) in the very position as found in the chosen collection site within the body. A cap (168) for the tissue collection chamber (166) is also shown.

Tissue collector (166), which can accommodate the various instruments herein described, can also be marked as appropriate for indicating the orientation of the tissue specimen. For instance, either or both distal end (174) or proximal end (176) of the collector (166) or cap (168) may be marked with words such as "top", "bottom", "front" and "rear" or the like; symbols may be used as well. Likewise, one or more sides of the collector (166) may be marked to indicate tissue orientation as shown in FIG. 3. Although not shown, cap (168) could alternately be located on the opposite end of collector (166), or collector (166) could have two caps.

Additionally, a label (170) may be placed on the tissue collector (166) to indicate particular information about the specimen, the patient, or the conditions of the procedure; e.g., identification number/name of patient, physician, date of procedure, left or right breast, special instructions, etc.

Tissue collection chamber assembly may have at least one port (172) to accommodate the various instruments herein described, as well as a tissue specimen. Port (172) is aligned with tissue collection chamber (166) so that a tissue sample may enter chamber (166) therethrough. Either or both distal or proximal ends (174) and (176) of chamber (166) may define a port (172) for the same purpose as described above.

Either or both tissue collection chamber assembly (162) and tissue collection chamber (166) may be partially or wholly transparent to x-ray or other energy so that the instruments and tissue specimens may be visible therethrough.

Trocar And Localization Wire

The trocar used in this assemblage is preferably one which fits within the inner lumen of the tubular tissue removal member. This permits the trocar to carry that member as it penetrates the outer skin and the tissue on the pathway to the selected site. The trocar used in this invention may simply be one having a sharp mechanical cutting surface or may be connected to one of any of known RF sources which generates energy for cutting tissue and, perhaps, cauterizing it as the initial incision is made.

Figure 4A:
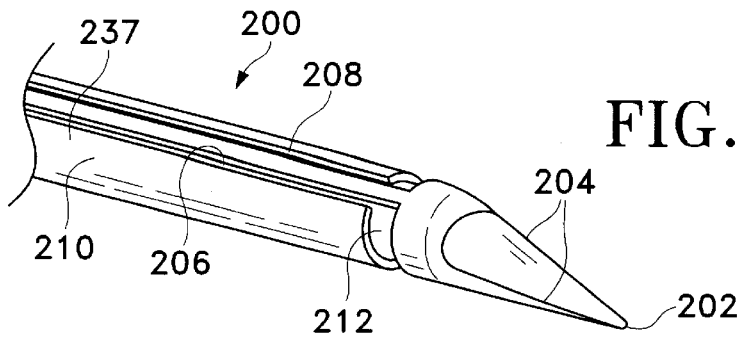
FIGS. 4A–4E show various embodiments of a trocar which fits within the tissue removal member and supports the tissue cutting member as it is introduced into the target tissue region.

FIG. 4A shows a typical, but desirable, variation of a trocar (200) which is especially suitable for use in this assembly. Specifically, trocar (200) has a sharp leading pointed end (202), a sharp cutting edge (204) and, desirably, two longitudinal grooves (206) and (208) extending along a portion or all of the exterior surface (210) of trocar (200). Grooves (206) and (208) are sized to accommodate shafts (402) and (404) (not shown) when trocar is extended through tissue removal member (140) so that a low-profile configuration may be accomplished to allow deployment of trocar (200), shafts (402) and (404), and cutting member (300) (not shown) in a smooth fashion.

Additionally, trocar (200) may contain one or more transverse slots (212) for carrying the cutting member to the selected tissue site. Slot (212) can extend partially along exterior surface (212) of trocar (200), in conjunction with another slot, or extend completely around trocar (200) to hold the entire cutting ring (300).

Figure 4B:
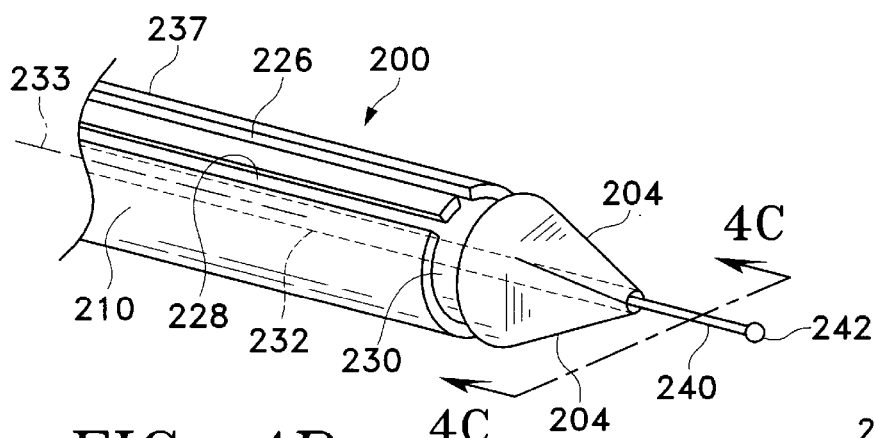
Figure 4C:
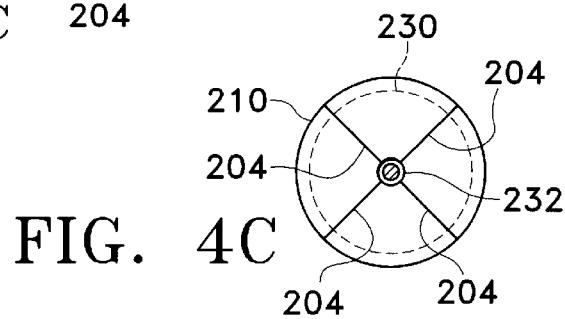

FIGS. 4B–4C show another desirable variation of trocar (200). Here, the trocar contains two longitudinal grooves (226) and (228) along with slots or grooves (230) for carrying cutting ring and its shafts as described above.

However, trocar (200) additionally contains an aperture (232) defined in the interior of the trocar along the trocar longitudinal axis (233). This aperture (232) is for the containment and passage therethrough of a localization wire (240).

Localization wire (240) is used as conventionally known to locate the tissue lesion or specimen to be excised during the initial phase of the excision process. Localization wire (240) is preferably made from titanium, nickel, stainless steel, tantalum, tungsten, or cobalt, and alloys thereof, and more preferably stainless steel or a nickel-titanium alloy. Wire (240) preferably has a diameter of between about 0.005 inch to about 0.050 inch, and more preferably has a diameter of between about 0.010 inch and about 0.025 inch (aperture (232) is sized to accommodate wire (240)). If not comprised of a radiopaque material, wire (240) is at least partially radiopaque. Radiopaque distal tip (242) facilitates tissue location and assists the physician user in operating the inventive device.

Wire (240) can extend proximally through a tissue removal member, collection chamber and assembly, and even through a controller box or drive unit (700) for automated or manual manipulation. Wire (240) is freely axially moveable within trocar (200) and the other devices described above.

Slightly different slots (230) are shown in FIGS. 4B–C for accommodating cutting member (300). Also shown are four cutting edges (204) for separating tissue.

Figures 4D, 4E:
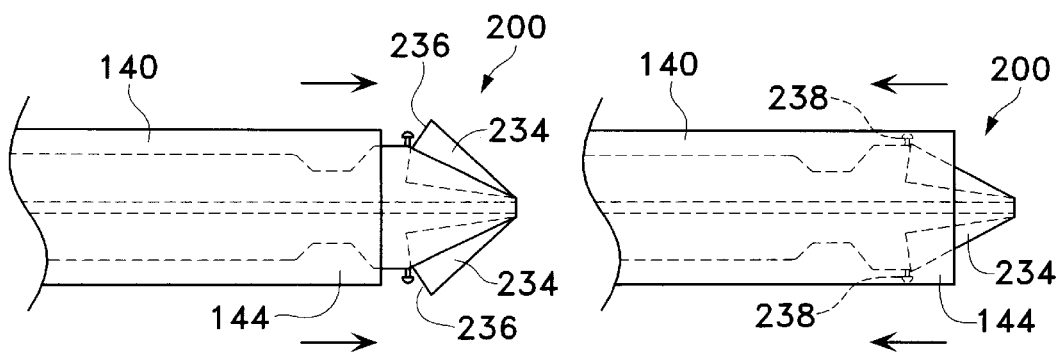

FIGS. 4D–E show a desirable configuration for trocar (200). Here sharp cutting edges consist of a collapsible blade (234) which is biased, by a spring or any other suitable means (not shown), to assume an extended, deployed position for cutting tissue. This extended position will be the natural position for the blade (234) when the trocar (200) is extended distally out the distal end (144) of tubular tissue removal member (140).

Upon proximal retraction of trocar (200), as shown in FIG. 4E, blade (234) proximal end (236) will engage distal end (144) of tissue removal member (140) and force blade (234) to retract into trocar (200) and lock against an optional locking pin (238) (or other suitable means such as a notch or latch) into trocar (200), allowing trocar (200) to further move proximally into tissue removal member (140). Likewise, distal movement of trocar (200) out distal end (144) of member (140) frees blade (234) to assume its biased, deployed position as shown in FIG. 4D. Locking pin (238) is not necessary for the operation of the trocar (200) of FIGS. 4D–E; blade (234) can stay retracted entirely by engagement with distal end (144) of member (140).

Trocar (200) can be made partially or entirely of stainless steel, nickel, titanium, cobalt, tungsten, or alloys thereof. In addition, proximal end (237) of trocar (200) can be optionally made of any suitable biologically inert plastic and joined to the distal end by any suitable means.

Access and Cutting Members

The cutting members discussed herein are all similar in that each have a cutting surface, i.e., the portion of the device which meets the tissue and cuts a path whether that path is made by a mechanical cutting as with a knife blade or if the separation is made by an RF or ultrasound energy source. The cutting member may be attached to an RF or ultrasound source or may be made up of mechanical cutters or may be combinations of those. Often, the members are mechanically vibrated or rotated to produce a cutting motion. The tissue itself can also be vibrated to produce a differential motion between the tissue and the cutting surface to create a mechanical cutting motion.

FIGS. 5A–5C show perspective, side, and end views, respectively, of a particularly useful configuration for cutting member (300) and access members (402) and (404) where the cutting member (300) is in its expanded condition. Specifically, FIG. 5A shows a ribbon cutting member (300) fixed at each of its first (302) and second ends (304) to shafts, or access members (402) and (404). Cutting member (300) may be affixed to access members (402) and (404) by any suitable means, such as welding, soldering, brazing, adhesive or mechanical fastening means such as crimping and the like; likewise, cutting member (300) may be integrally formed with access members (402) and (404) so as to preclude the need for joining them together.

Access members (402) and (404) may comprise a shaft, wire or rod (as shown in FIGS. 5 and 6), hollow or solid, or they may take other forms as suitable for achieving their intended purpose as described in detail below. Access members may be fabricated from various alloys, such as stainless steel, or metals such as titanium, platinum, tantalum, cobalt, nickel, other suitable biologically inert metals or their alloys. Especially desired are radiopaque materials, such as stainless steel or platinum and its alloys. In addition, access members (402) and (404) may also comprise biologically inert polymeric or organic materials or mixtures thereof. If access members (402) and (404) comprise a metal or metal alloy, it is desirable that one or both members be fully or partially coated with, or inserted within, a polymeric layer or member. Such a layer serves to insulate the access members (402) and (404) from RF energy if it is utilized.

When compared to FIGS. 5A–5C, FIGS. 6A–6C illustrate the desired operation of access members (402) and (404) in conjunction with cutting member (300). First access member (402) is desirably, though not necessarily, rotatably fixed so that it is not capable of rotation about its longitudinal axis (406). This may be accomplished in a variety of ways. For instance, it may be manually held from rotating by the physician user, or it may be permanently or releasably fixed in controller box (700) or other suitable apparatus. As a result of being fixed, first access member (402) acts to hold the first end (302) of cutting member (300) fixed in space with respect to the first access member longitudinal axis (402). This provides a reference point upon which the physician user may rely to accurately place the tissue removal assembly, and most importantly, cutting member (300), at the precise location of the tissue to be excised.

Second access member (404) desirably is free to rotate about its longitudinal axis (408). The axial rotation of second access member (404) may be accomplished and controlled in a variety of ways, the scope of which is not limited by the following examples. For instance, axial rotation may be directly controlled manually by the physician user, or it may be indirectly controlled via controller box (700). Such a control device could be activated manually, hydraulically, or electronically, for instance, by a dial, button, switch, or the like. Such a control device preferably allows the physician user to incrementally control the degree of axial rotation of second access member (404) depending on a variety of factors such as the preferred diameter of the tissue sample to be cut, as will be discussed in greater detail below.

As shown in FIGS. 6A–6C, axial rotation of second access member (404) results in a likewise rotation of the second end (304) of cutting member (300), to which the distal end of second access member (404) is affixed. As rotation continues beyond 360°, second end (304) of cutting member (300) continues to turn in with respect to the first end (302) such that the diameter D (FIG. 5C) of cutting member (300) is effectively reduced to D' (FIG. 6C). The degree of rotation is limited only by the physical limits imposed by cutting member (300), so that theoretically second access member (404) may rotate through several complete or partial turns, resulting in a tightly wound and constricted cutting member (300), whose diameter D' is now notably smaller than its original diameter D.

The rotatability of second access member (404) and, in turn, second end (304) of cutting member (300) is critical to the cutting action of the removal assembly, especially in cutting off a distal end of the tissue specimen, such as when the device is used with RF energy.

Although it is desirable that first access member (402) be fixed as described above, first access member (402) can also be free to rotate about its longitudinal axis (406) in the same manner as described above with respect to second access member (404). In this manner, it is desirable that second access member (404) likewise be rotatably fixed about its longitudinal axis (408) as described above. However, it is not absolutely necessary that one access member be rotatably fixed while the other is not; both access members can simultaneously be rotatably fixed or both may be free to rotate about their respective longitudinal axes.

Further, when not attached to tubular tissue removal member (140), both first and second access members (402) and (404) are, independently or jointly, moveable in all other directions and modes, such as axial translation in a direction parallel to their respective longitudinal axes, lateral translation in any direction not parallel to the same axes, or rotation about any orthogonal axis (not shown), for example. This allows for free movement of the independent components of the tissue removal assembly by the physician user during operation.

Finally, independent of any of the capabilities mentioned above, both first and second access members (402) and (404) are jointly axially rotatable about an axis (410) defining the center of the cutting ring (300). As the device is moved forward to the distal end of a tissue specimen, this capability allows the physician user to rotate the entire assembly so to assist them in cutting off the distal end of the tissue specimen and excising it from the body.

Turning now to the cutting member (300), FIGS. 7–10 depict exemplary configurations for a cutting member (300) that can be used to cut the desired tissue sample by RF energy, ultrasound energy, mechanically, or any combination thereof.

Figures 7A, 7B:
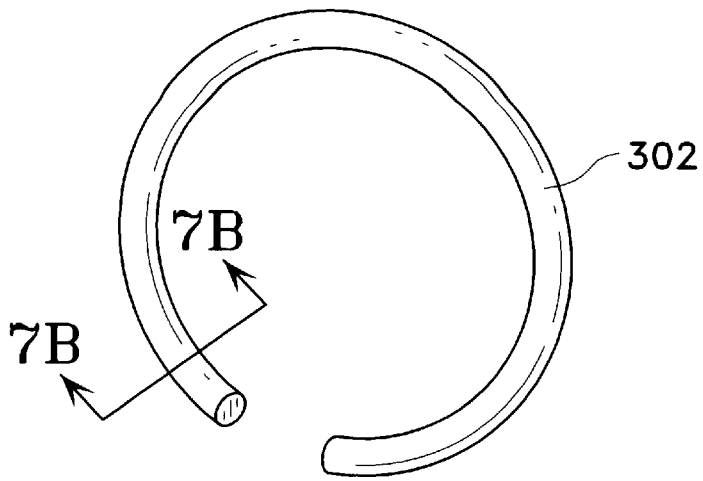
FIGS. 7A to 7B show perspective and cross-sectional views of a wire cutting member in an expanded configuration.

FIGS. 7A and 7B depict a simple configuration where the cutting member (302) has a generally round cross-section. When this configuration is used, the cutting member may be a solid or hollow wire, shaft, rod, ribbon, or other shape approximating a generally round, oval, or square cross section. This configuration is especially suitable for RF cutting.

Figures 8A, 8B:
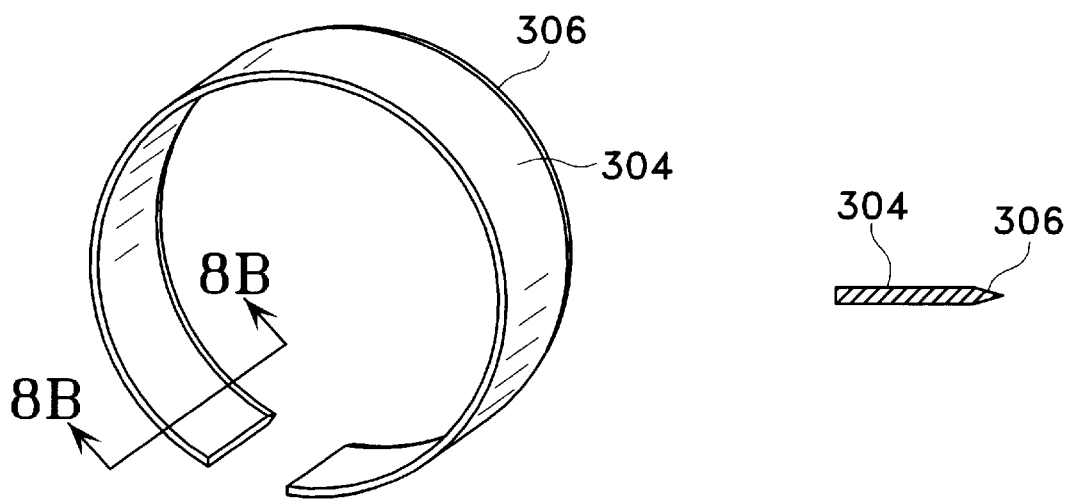
FIGS. 8A to 8B show perspective and cross-sectional views of a ribbon cutting member, having a leading edge knife-edge cutting surface, in an expanded configuration.

FIGS. 8A and 8B depict a ribbon cutting member (304) having a generally rectangular cross section and a single knife-edge cutting surface (306). This cutting surface (306) assists in cutting tissue upon rotation and axial translation of cutting member (304) with respect to the tissue to be excised. When used in conjunction with RF energy, a sharpened knife edge cutting surface (306) will focus the RF energy towards the leading edge of the cutting surface and facilitate movement of the device through the tissue and to cut off the distal end of the tissue specimen. Cutting surface (306) can be on either side of cutting member (304).

FIGS. 9A and 9B show a ribbon cutting member (308) having a generally rectangular cross-section and a serrated cutting surface (310) that may be particularly useful in combination with a rotating action or vibratory cutting when in conjunction with RF or ultrasound energy. This further limitation of surface area on the leading edge of the cutting member enhances the use of RF energy in the cutting member of the inventive device. Serrated cutting surface (310) can be on either side of cutting member (308).

FIGS. 10A and 10B show a cutting member (312) having an optional serrated cutting surface (316) extending in a direction generally perpendicular from the surface of the cutting member (312). This serrated cutting surface (316) can be used to assist in cutting tissue in a plane generally perpendicular to the length of the tissue specimen, especially as the cutting member (312) is expanded by the rotation of second access member as previously described. Such a cutting surface (316) can also be a smooth knife-edge, and can be used in conjunction with one or more cutting surfaces, such as knife-edge cutting surface (314). Although not shown in FIGS. 10A and 10B, a similar serration can additionally or singly exist on the opposite interior surface (318) of cutting member (312).

The ribbon cutting member (300), although shown in FIGS. 8–10 as having some type of knife-edge or serrated cutting surface, need not have such a cutting surface at all. This is especially true when cutting member (300) is used with RF energy to cut through tissue. In addition, other cross-sectional shapes and cutting surface configurations may be used in the tissue removal assembly.

The material making up the cutting members shown in FIGS. 7 through 10 is not central to this invention. The materials may be any of a variety of stainless steels, cobalt, tungsten, titanium, nickel, tantalum, and other alloys typically used in this service.

Nonetheless, we have found that certain nickel-titanium alloys are particularly suitable for use with this device, due to the requirement that cutting member (300) be capable of performing under the conditions of repeated expansion and contraction by high radius of curvature bending (i.e. rolling and unrolling the device) via axial rotation of second access member (404) without inducing strain upon the cutting member material. This is also particularly true when the blades are used either as simple knife edge cutters or as a combination of RF/mechanical cutters. This material is typically a 50/50 molar ratio alloy of titanium and nickel; however, other ratios are within the scope of the invention. Closely related alloys are the shape memory alloys which exhibit superelastic/pseudoelastic shape recovery characteristics. These alloys are well-known and are commonly referred to as "nitinol." See, for instance, U.S. Pat. Nos. 3,174,851, 3,351,463, and 3,753,700, the entirety of which are hereby incorporated by reference. These alloys are characterized by their ability to be transformed from an austenitic crystal structure to a stress-induced martensitic (SIM) structure at certain temperatures, and return elastically to the austenitic shape when the stress is removed. These alternating crystalline properties provide the alloy with its super-elastic properties. The nitinol forms of these alloys are readily commercially available and typically will undergo the austenite-SIM-austenite transformation at a variety of temperature ranges between −20° C. and 30° C.

Tissue Manipulation Devices

Figure 11A:
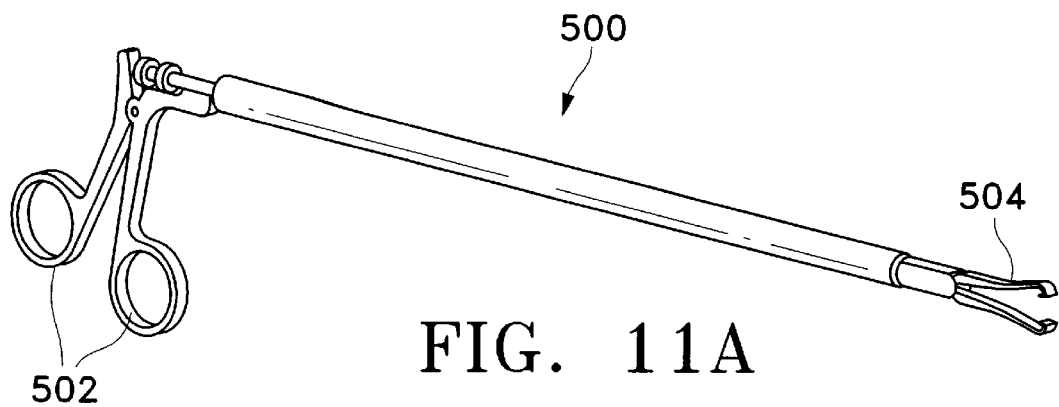
FIG. 11A is a side view of a typical endoscopic snare suitable for use in grasping the removed tissue in accordance with this invention.
Figure 11B:
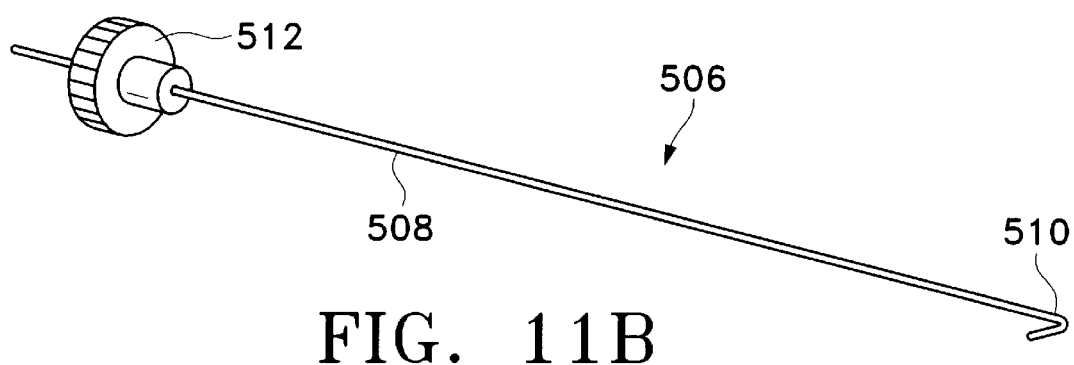
FIG. 11B shows a harpoon spear which is also suitable for accessing and grabbing tissue for use in removing selected tissue when using this device.
Figure 11C:
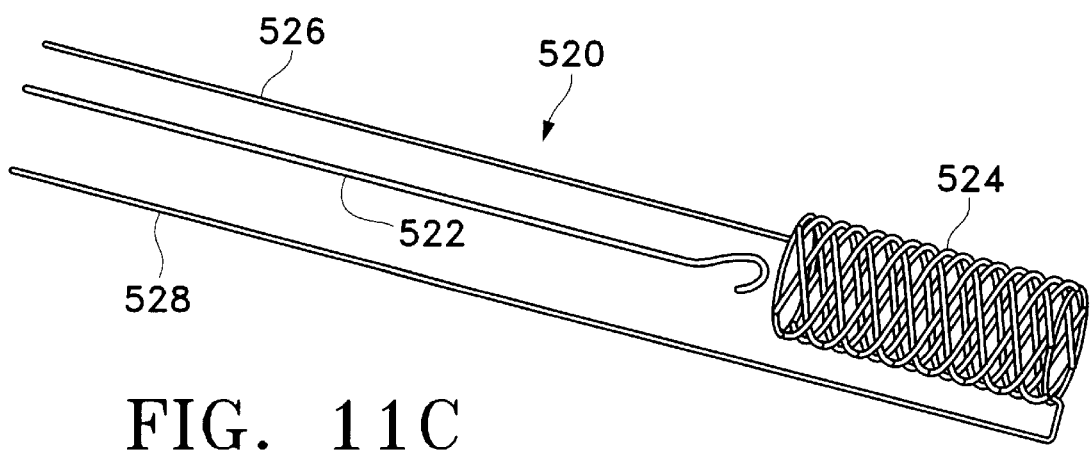
FIG. 11C is an expandable braid and optional allied hook also suitable for retrieving tissue using this invention.

FIGS. 11A through 11C show tissue manipulation devices as may be used in conjunction with the overall assembly. In some instances, it may be desirable to grasp the initial portion of excised tissue so to guide it through the tissue removal member. Depending on which of the configurations of tissue removal member is selected, a choice of one of the noted devices may be appropriate.

FIG. 11A shows a simple endoscopic grasping device (500) which is readily available on the commercial market. Movement of the scissor-like handle produces a corresponding movement on the grasping tongs (504).

FIG. 11B shows a tissue manipulation device (506) having a small wire-like shaft (508) and a harpoon-like end (510). For the purposes of completeness only, a manipulation knob (512) is also included for view.

FIG. 11C shows a combination of a braided grasper (520) and a hook component (522). The braided tissue snaring device (520) includes a distal woven braid section (524) which is easily manipulated by the two control wire or rods (526) and (528). If necessary, hook (522) is used to pull the excised tissue into braided cage (524) or to push the braided cage over the excised tissue. The two control wires (526) and (528) are used to either expand the diameter of braided cage (524) or to make that diameter smaller. Once the tissue is at least partially within the braided cage (524), the device is removed from the lumen of the tissue removal device.

Other devices for removing excised tissue from the selected site, such as vacuum or suction assisted removal, would certainly be appropriate.

Peel-Away Sheath

Figure 12:
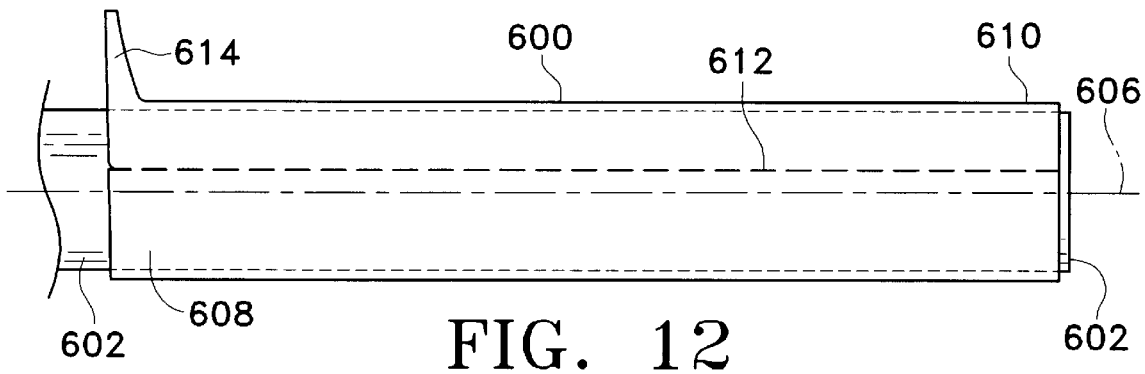
FIG. 12 shows a peel-away sheath covering for the expandable tubular tissue removal member.

A desirable but optional feature of the present invention is shown in FIG. 12 as sheath (600). Sheath (600), in its most general sense, is a thin covering or tube designed to fit over the exterior surface of expandable tubular tissue removal member (602) and to hold member (602) in a collapsed, non-expanded position prior to excision and removal of tissue. This ensures tissue removal member (602) maintains a low profile during the tissue accession steps. Sheath (600) also acts to provide additional axial, longitudinal, and torsional rigidity to member (602). Sheath (600) may be used with any of the designs herein described. Sheath (600) is desirably comprised of a biologically inert polymer; accordingly it can comprise any of the materials described herein or their equivalents.

Preferably, sheath (600) contains at least one perforation (612) running along all or a portion of the length of sheath (600) in a direction parallel to the sheath longitudinal axis (606) from its proximal end (608) towards its distal end (610). Perforation (612) allows the physician user to remove, or peel away, sheath from tissue removal member (602) during use so that member (602) may radially expand. An optional handle is (614) located at or near the proximal end of sheath (600) to facilitate removing, or peeling away, sheath (600) at perforation (612).

Tissue Separating Member

Figure 13A:
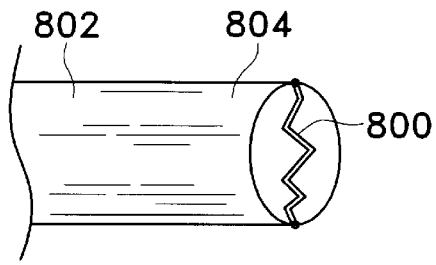
FIGS. 13A through 13F show partial perspective and side views of variations of the invention having a tissue separation member.
Figure 13C:
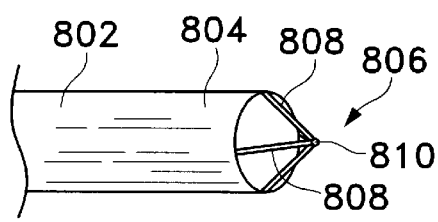
Figure 13B:
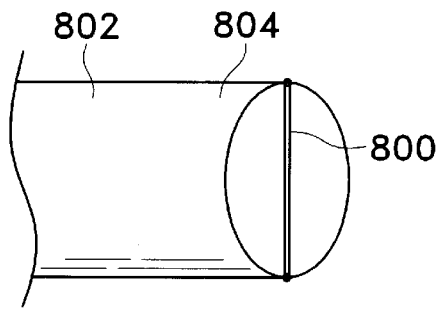

FIGS. 13A–13B shows an optional tissue separating member (800) spanning the diameter of the distal end (804) of expandable tubular tissue removal member (802). Separating member (800) desirably is extensible such that when tissue removal member (802) is in a radially collapsed position, as shown in FIG. 13A, it bends or collapses to assume a first position. This position is not important; i.e., it may be due to separating member containing foldable joints, taking on a spring form, or bowing in a proximal or distal direction with respect to tissue removal member distal end (804), as long as separating member (800) is capable of performing its function described below.

FIG. 13B shows separating member (800) in a second, extended or expanded configuration where it is generally straight as it spans the tissue removal member distal end (804) diameter. This is the position achieved when tubular tissue removal member is radially expanded. In all the embodiments, separating member (800) can take the form of a spring, hollow or solid wire or rod, a ribbon or ribbon-like braid, etc. It may be comprised variously of any of the metals or alloys herein described, although it is preferably comprised of a nickel-titanium alloy. Separating member (800) is used in the following manner with any of the variations of the inventive device described herein: as tissue removal member (802) and/or cutting ring is moved forward to excise a tissue specimen, the distal end (804) approaches the tissue specimen. Rather than assimilating the entire tissue specimen whole into the tissue removal member (802), it may be desirous to further cut the tissue specimen into two or more additional pieces so that each or all may be sequentially or simultaneously removed from the body. Separating member (800) accomplishes this by cutting the tissue specimen as it passes proximally through the distal end of tissue removal member (802).

Accordingly, separating member (800) may comprise a mechanical blade with one or more sharp cutting surfaces, it may be attached to an RF energy source via a wire (not shown) or the fixed access member described above, it may be attached to an ultrasound energy source, a mechanical vibration or oscillation source, or any combination thereof. Separating member (800) can even be connected to a manual or automated deploying force so to assist its expansion from the first, collapsed configuration to the second, expanded configuration.

Figure 13D:
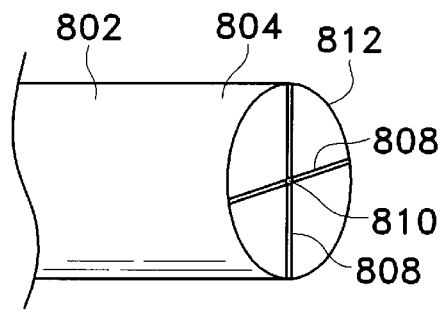

Tissue separating member is shown in FIGS. 13A–13B as a single member obviously only capable of cutting an excised tissue specimen into two separate pieces and rotating at the tissue distal end to excise the tissue from the body. It is within the scope of the present invention for the separating member to contain any number of additional members for cutting the tissue specimen into three or more pieces. An example of this is shown in FIG. 13C, wherein separating member (806) comprises a plurality of cutting elements (808) connected at distal pivoting connecting point (810). FIG. 13C shows this embodiment in a collapsed configuration while FIG. 13D shows member (806) in its second, expanded configuration. An optional cutting surface (812) on distal end (804) can also be used to cut tissue.

Figure 13E:
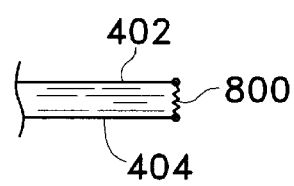
Figure 13F:
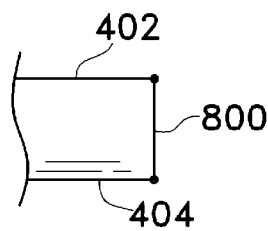

FIGS. 13E and 13F, respectively, show collapsed and expanded versions of separating member (800) without any tissue removal member. This is a simple yet desirable configuration, in which separating member (800) is connected at each end to the distal end of access members (402) and (404).

In all its embodiments, tissue separating member (800) may be used in conjunction with the ring cutting member (300) or alone to achieve the desired result of excising and cutting a tissue specimen, including rotating to cut the tissue specimen distal end, from the body. Member (800) may be used variously with or without RF energy. In addition, tissue may be pulled proximally through separating member (800) to separate or cut tissue as opposed to pushing the device distally through the tissue.

Controller Box

As shown generically in FIG. 1, controller box or driver unit (700) is a preferable component of the present invention. In addition to the functions described above, controller box may serve various other functions such as providing a source of RF energy, a source of ultrasound energy, a source of mechanical energy, and the like. Mechanically, controller box (700) provides variously for rotation, translation, and vibration of cutting member (300), expansion and contraction of ring (300) and/or tubular tissue removal member (100). It serves as a connecting site for the variously described energy sources to the inventive device, and can be automated to any desirable degree to assist the physician user to properly and safely use the invention. As generically described, it is appreciated that controller box (700) may additionally contain other features or perform other functions as necessary for the proper and safe use of the invention. An example of a device having such functions is found in U.S. Pat. No. 5,526,822, which is hereby incorporated by reference.

Procedure for Use

FIGS. 14A through 14F show a generic method for using the tissue removal assembly of this invention. For the purposes of illustration, this description assumes that the user is removing a lesion found in breast tissue. The lesion (900) is found behind skin surface (902). Surrounding tissue is also shown. The generic device found in FIG. 1 is used for purposes of this description with the exception that tissue removal member (100) is in a simpler configuration consisting of only a single, expandable tubular member and that cutting member (300) is attached to the distal end of tissue removal member (100). The use, however, according to this invention is not significantly different when other variations of the device are used.

Figure 14A:
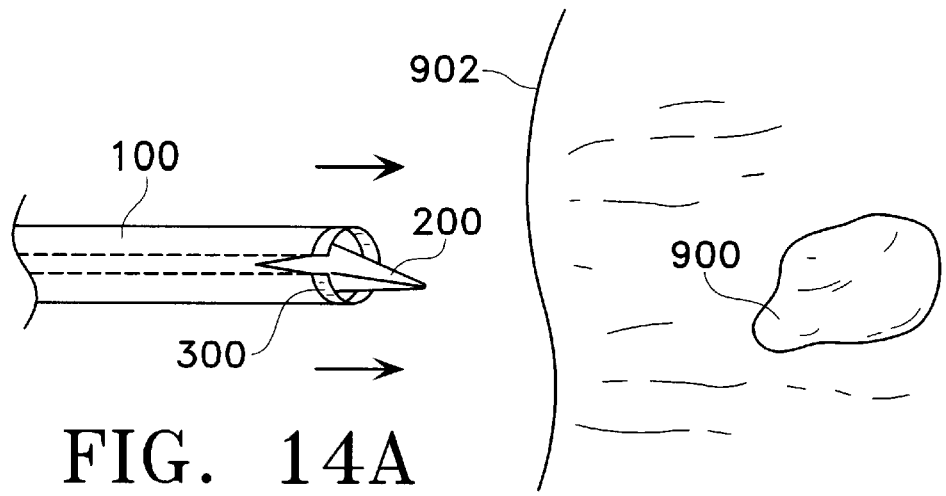
FIGS. 14A through 14F show a typical procedure sequence using the invention described herein.

FIG. 14A shows the assembled device ready for introduction to the skin surface. Shown is the expandable tissue removal member (100) and trocar (200) with the attached cutting member and attached first and second access members (shown in dashed lines) not yet inserted in the proximal end of the tissue removal member (100). The device is positioned at the skin surface so that when the cutting member and expandable tissue removal member (100) expanded to its full diameter by axial rotation of second access member, the lesion (900) is within a circumference corresponding to that diameter. Tip (242) of localization wire (240) is also shown extending from trocar (200).

Figure 14B:
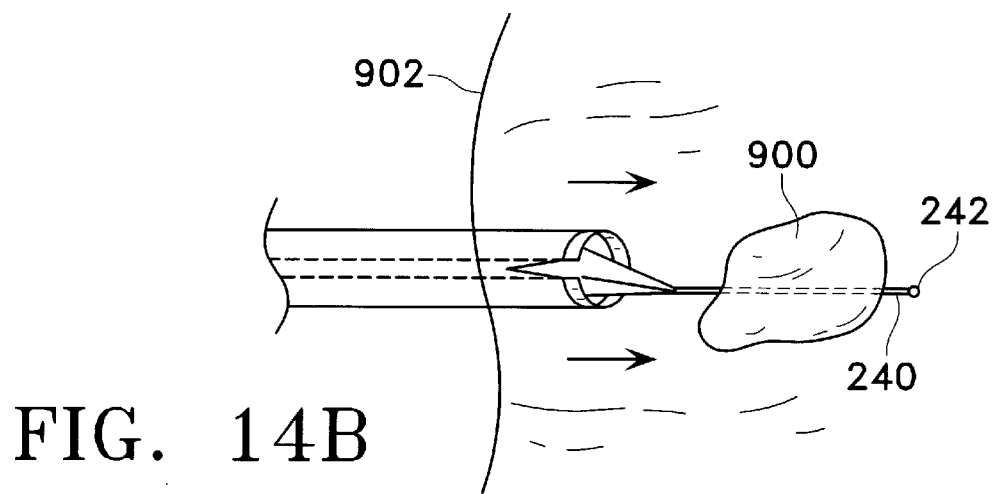

FIG. 14B shows the assembled device after localization wire (240) has been extended completely through the lesion (900) under stereotactic guidance, and the trocar (200), tissue removal member (100) with cutting member and access members have penetrated the skin surface (902) and are approaching lesion (900).

Figure 14C:
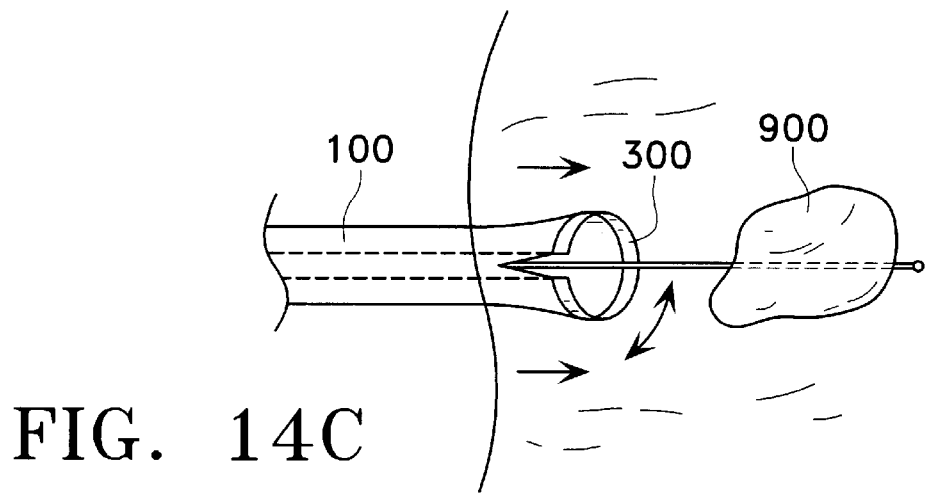

FIG. 14C shows the initial expansion of the collapsed cutting member (300) and the distal end of tissue removal member (100). This variation shows the use of an RF powered cutting member (300). A mechanical or ultrasound cutter may obviously be employed as well or instead of an RF-style cutter (300). The cutting member (300) and removal member (100) is first extended to the section of tissue distal to the lesion through the path cut by trocar (200) in a collapsed configuration. RF power is then applied to the cutting member (300), which is next rotated by a rotatable access member, after removal of optional sheath (600) (not shown), so to form a circular cut distal to lesion (900). This circular cut will be the end of the cylinder of tissue which is ultimately removed.

Figure 14D:
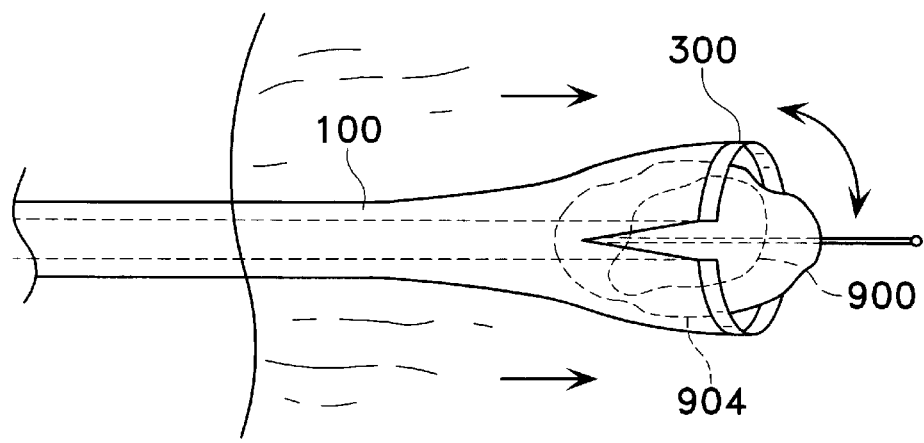

FIG. 14D shows axial movement of the cutting member (300) and the generally cylindrical tissue mass (904) formed as the cutting member (300) is simultaneously optionally rotated until the cutting member (300) is past lesion (900) during application of RF energy.

Figure 14E:
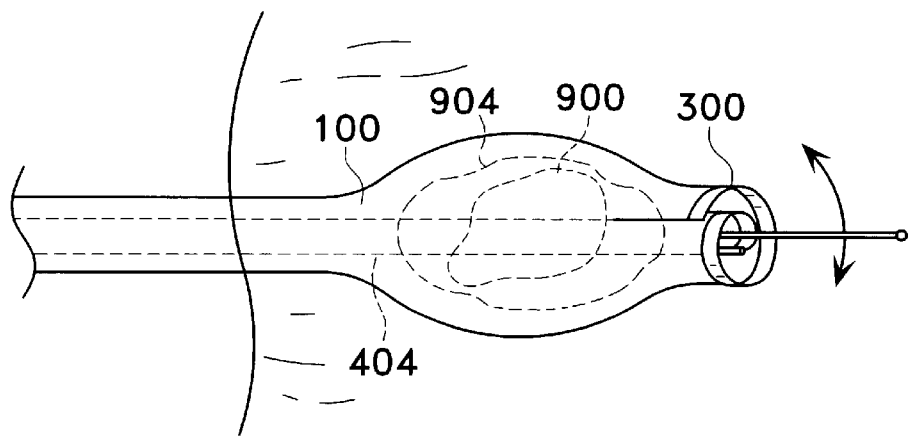

FIG. 14E shows the collapsing and simultaneous rotation of cutting member (300) by axial rotation of second access member (404) during application of RF energy so to cut the tissue distal to lesion (900) and allow the physician user to remove the newly formed cylindrical tissue mass (904) surrounding lesion (900) from the breast.

Figure 14F:
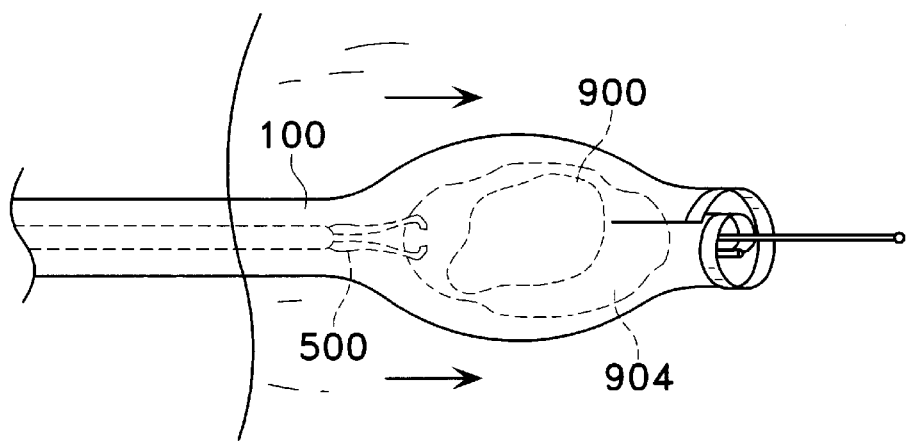

FIG. 14F shows the introduction of grasping member (500) to the distal end of the cylindrical tissue mass (904) containing lesion (900) and the removal of the cylindrical tissue mass (904) through the lumen of tissue removal member (100). In this instance, tissue removal member (100) is braided and radially expandable so to accommodate a tissue mass (904) which has a significantly larger diameter than its own diameter. This is a particularly attractive feature of the invention that obviates the need for making a large incision to remove a relatively large tissue mass (904). The tissue mass (904) may be cut into two or more additional pieces as it enters the tissue collection chamber by one or more tissue separating members (not shown).

The entire assembly may then be removed from the incision or may be used to excise additional tissue from the site. Note that the tissue volume depicted in FIGS. 14A–F is generally football-shaped as is appropriate. However, especially when used with RF, a tissue specimen shape generally approximating a right cylinder is possible.

Ultrasound energy may also be utilized to assist in the cutting action of the cutting member (300). For instance, a source of ultrasound energy may be included in controller box (700), for instance, and selectively transmitted, alone or in conjunction with mechanical or RF-assisted cutting, to vibrate the cutting member (300) and surrounding tissue to facilitate cutting the tissue sample.

When used solely or in conjunction with mechanical cutting or ultrasound, RF energy may be utilized in the frequency range of about 500 Hz to about 500 KHz to assist in cutting the desired tissue. The appropriate power setting, frequency, and waveform may be selectively chosen by the physician user or automatically preset or selectable through controller box (700) or any commercially available RF controller device.

Alternatively, or in addition to RF cutting, RF energy can be selectively used to cauterize the cut tissue in the remaining cavity in the vicinity of the excision margin to minimize trauma, control unnecessary bleeding, and to prevent hemotoma formation. An example of the use of RF energy for such an application is more thoroughly described in U.S. Pat. Nos. 5,085,659, 5,569,244 and 5,578,030, the entirety of each hereby incorporated by reference. This can be done not only during the tissue accession and removal steps, but after the tissue specimen is removed from the body. In addition to or instead of using the present inventive device for such cautery, any typical electrocautery probe as is well-known in the art may be used.

Prior to, during, or after such cauterization, the remaining cavity may be examined with an endoscope or other appropriate viewing device so to assist the user physician in locating bleeders. Once the physician user is satisfied that the remaining cavity is properly cauterized, the cavity may be alternatively packed with appropriate biologically inert packing material, such as a fibrin-collagen matrix, to further prevent unnecessary bleeding, minimize the possibility of hemotoma formation, and to help prevent dimpling or deformation of the breast.

The entire procedure can be accomplished while the patient is under local anesthesia. The device is capable of being utilized stereotactically or under ultrasound guidance. In addition, the device is capable of computer control so that even more precise operation may be accomplished.

The invention herein has been described by examples and a particularly desired way of practicing the invention has been described. However, the invention as claimed herein is not loaded to that specific description in any manner. Equivalence to the description as hereinafter claimed is considered to be within the scope of protection of this patent:

We claim as our invention:

1. A tissue removal assembly, comprising:
 a cutting member, moveable between a collapsed first position and an expanded second position, the cutting member having a first end, a second end, and at least one cutting surface;
 a first access member having a longitudinal axis, a proximal end and a distal end, the distal end of which is fixed to the first end of the cutting member; and
 a second access member having a longitudinal axis, a proximal end and a distal end, the distal end of which is fixed to the second end of the cutting member;
 the second access member axially rotatable about the longitudinal axis so that axial rotation of the second access member will move the cutting member between the collapsed first position and the expanded second position.

2. The tissue removal assembly of claim 1 additionally comprising:
 a tubular tissue removal member having a proximal end, a distal end, an interior surface, an exterior surface, a longitudinal axis, an open, distally located tissue entry opening; a relatively more proximal, tissue exit port, and a tissue removal passageway extending between the proximal and distal ends.

3. The tissue removal assembly of claim 2 where the tissue removal member is configured to accommodate the cutting member and the first and second access members in the axial passageway when the cutting member is in the collapsed first position, and where the cutting member is extendible through the tissue entry opening.

4. The tissue removal assembly of claim 1 where the cutting surface is configured to cut a substantially cylindrical path through discrete tissue mass.

5. The tissue removal assembly of claim 2 where the cutting member is manually manipulatable from the proximal end of the tubular tissue removal member.

6. The tissue removal assembly of claim 1 where the cutting member is at least partially radio-opaque.

7. The tissue removal assembly of claim 1 where the cutting member is a wire cutting member.

8. The tissue removal assembly of claim 7 where the cutting surface is serrated.

9. The tissue removal assembly of claim 1 where the cutting member is a ribbon cutting member having a leading edge, a trailing edge, and a ribbon surface.

10. The tissue removal assembly of claim 9 where the cutting surface of the ribbon cutting member is the leading edge.

11. The tissue removal assembly of claim 10 where the leading edge is serrated.

12. The tissue removal assembly of claim 10 further comprising a second cutting surface on the ribbon surface.

13. The tissue removal assembly of claim 12 where the second cutting surface is serrated.

14. The tissue removal assembly of claim 1 where the cutting member comprises a material selected from the group consisting of titanium, nickel, stainless steel, cobalt, tantalum, tungsten, and alloys thereof.

15. The tissue removal assembly of claim 1 where the cutting member comprises titanium and nickel.

16. The tissue removal assembly of claim 1 where the cutting member is a radio frequency cutter utilizing radio frequency energy to cut discrete tissue mass.

17. The tissue removal assembly of claim 16 further comprising a radio frequency source connected to the cutting member, the radio frequency source being suitable for cutting discrete tissue mass.

18. The tissue removal assembly of claim 1 where the cutting member is a mechanical blade.

19. The tissue removal member of claim 18 further comprising a mechanical energy source connected to the cutting member, the mechanical energy source being suitable for cutting discrete tissue mass.

20. The tissue removal member of claim 18 where the mechanical blade cutting member is mechanically vibrated to cut discrete tissue mass.

21. The tissue removal member of claim 18 where the mechanical blade cutting member is rotated to cut discrete tissue mass.

22. The tissue removal assembly of claim 1 where the cutting member is a radio frequency cutting member having a sharp mechanical cutting surface.

23. The tissue removal assembly of claim 1 where the cutting member is an ultrasound cutter utilizing high frequency audio energy to cut discrete tissue mass.

24. The tissue removal assembly of claim 23 further comprising an ultrasound source connected to the cutting member which is suitable for cutting the discrete tissue mass.

25. The tissue removal assembly of claim 2 further comprising a localization wire sized to fit within the tissue removal passageway and is extendable through the tissue entry opening located in the tubular tissue removal member.

26. The tissue removal assembly of claim 25 where the localization wire is at least partially radiopaque.

27. The tissue removal assembly of claim 25 where the localization wire comprises a material selected from the group consisting of titanium, nickel, stainless steel, cobalt, tantalum, tungsten, and alloys thereof.

28. The tissue removal assembly of claim 25 where the localization wire comprises titanium and nickel.

29. The tissue removal assembly of claim 2 further comprising a sheath removably affixed to the exterior surface of the tubular tissue removal member, the sheath having a distal end, a proximal end, and a longitudinal axis.

30. The tissue removal assembly of claim 29 where the sheath is perforated in a direction parallel to the sheath longitudinal axis.

31. The tissue removal assembly of claim 30 additionally comprising a handle near the proximal end of the sheath to facilitate opening the sheath along the perforation.

32. The tissue removal assembly of claim 2 where the tubular tissue removal member further includes a shaft passageway exterior to the tissue removal passageway and generally parallel to the tubular tissue removal member longitudinal axis; and the cutting member, first access member, and second access members are slideable within and rotatable within the shaft passageway to advance the cutting surface.

33. The tissue removal assembly of claim 2 where the tubular tissue removal member further includes a shaft passageway interior to the tissue removal passageway and generally parallel to the tubular tissue removal member longitudinal axis; and the cutting member, first access member, and second access members are slideable within and rotatable within the shaft passageway to advance the cutting surface.

34. The tissue removal assembly of claim 2 where the cutting member is attachable to the distal end of the tubular tissue removal member.

35. The tissue removal assembly of claim 34 where the first and second access members are attachable to the tubular tissue removal member.

36. The tissue removal assembly of claim 35 where the tubular tissue removal member defines a longitudinal aperture, the aperture extending from the tubular tissue removal member distal end towards the tissue removal member proximal end; the aperture defining first and second tubular tissue removal member longitudinal edges.

37. The tissue removal assembly of claim 36 where the first and second access members are attachable to the tubular tissue removal member along at least a portion of the first and second tubular tissue removal member longitudinal edges.

38. The tissue removal assembly of claim 2 where the tubular tissue removal member defines a longitudinal aperture, the aperture extending from the tubular tissue removal member distal end towards the tissue removal member proximal end; the aperture defining first and second tubular tissue removal member longitudinal edges; and further comprising:

a cutting member support ring attachable to the distal end of the tubular tissue removal member, the support ring moveable between a collapsed first position and an expanded second position and having a first end, a second end, and a surface adapted for connecting to the cutting member;

a first support rod having a longitudinal axis, a proximal end, and a distal end attachable to both the first end of the support ring and the distal end of the tubular tissue removal member, the first support rod longitudinal axis attachable to the tubular tissue removal member along at least a portion of the first tubular tissue removal member longitudinal edge; and a second support rod having a longitudinal axis, a proximal end, a distal end attachable to both the first end of the support ring and the distal end of the tubular tissue removal member, the second support rod longitudinal axis attachable to the tubular tissue removal member along at least a portion of the second tubular tissue removal member longitudinal edge, the second support rod axially rotatable about the longitudinal axis so that axial rotation of the second support rod will move the support ring between the collapsed first position and the expanded second position.

39. The tissue removal assembly of claim 2 further comprising a tissue manipulation device locatable within the tissue removal passageway, said tissue manipulation device configured for removing excised discrete tissue mass.

40. The tissue removal assembly of claim 2 further comprising a manipulatable grasping tool locatable within the tissue removal passageway, said grasping tool configured for removing excised discrete tissue mass.

41. The tissue removal assembly of claim 40 where the manipulatable grasping tool comprises a pair of opposing jaws suitable for grasping excised discrete tissue mass.

42. The tissue removal assembly of claim 40 where the manipulatable grasping tool comprises a grasping braid suitable for grasping excised discrete tissue mass.

43. The tissue removal assembly of claim 2 further comprising a manipulatable suction tool locatable within the tissue removal passageway, said suction tool configured for removing excised discrete tissue mass.

44. The tissue removal assembly of claim 2 further comprising a trocar having an exterior surface, a distal section, a proximal section, and a longitudinal axis, the trocar sized to fit within the tissue removal passageway.

45. The trocar of claim 44 where the trocar defines a longitudinal aperture substantially extending along the trocar longitudinal axis.

46. The trocar of claim 44 further comprising at least one longitudinal groove extending along the surface of the trocar, the groove having a distal end and a proximal end.

47. The trocar of claim 46 further comprising at least one indentation located distally of the distal end of the groove.

48. The trocar of claim 44 where the distal section of the trocar comprises a material selected from the group consisting of titanium, nickel, stainless steel, cobalt, tantalum, tungsten, and alloys thereof, and where the proximal section comprises a biologically inert plastic.

49. The trocar of claim 44 where the distal end further comprises at least one retractable cutting surface biased to assume an extended first position and movable to a retracted second position.

50. The tissue removal assembly of claim 2 where the tissue removal member is at least partially radiopaque.

51. The tissue removal assembly of claim 2 where the tissue removal member is expandable.

52. The tissue removal assembly of claim 51 where the tissue removal member is braided.

53. The tissue removal assembly of claim 51 further comprising an extensible tissue separating member attachable to the distal end of the tubular tissue removal member.

54. The tissue removal assembly of claim 53 where the extensible tissue separating member is connected to a radio frequency source.

55. The tissue removal assembly of claim 54 where the extensible tissue separating member is connected to at least one of the first or second access members.

56. The tissue removal assembly of claim 54 where the extensible tissue separating member has a sharp cutting surface.

57. The tissue removal assembly of claim 53 where the extensible tissue separating member is a mechanical blade.

58. The tissue removal assembly of claim 2 additionally comprising a tissue collection chamber having a proximal end and a distal end for collecting excised discrete tissue mass.

59. The tissue removal assembly of claim 58 where the tissue collection chamber contains an external label for indicating information.

60. The tissue removal assembly of claim 58 where the tissue collection chamber contains markings on at least one of the distal or proximal ends for indicating the orientation of the excised discrete tissue mass.

61. The tissue removal assembly of claim 58 where at least one of the distal or proximal ends of the tissue collection chamber additionally defines a port; the port and tissue collection chamber each configured to accommodate the cutting member, first access member, second access member, and a tissue retrieval instrument.

62. The tissue removal assembly of claim 61 further comprising a tissue retrieval chamber assembly attachable to the tubular tissue removal member proximal end;

the tissue collection chamber assembly having at least one port to accommodate the cutting member, first access member, second access member, and a tissue retrieval instrument;

the tissue collection chamber assembly adapted to at least partially contain the tissue collection chamber.

63. The tissue removal assembly of claim 62 where the tissue collection chamber and tissue collection chamber assembly each are transparent to x-ray energy.

64. A radio frequency-assisted tissue removal assembly, comprising:

a cutting member, moveable between a collapsed first position and an expanded second position, the cutting member having a first end, a second end, and at least one cutting surface;

a first access member having a longitudinal axis, a proximal end and a distal end, the distal end of which is fixed to the first end of the cutting member;

a second access member having a longitudinal axis, a proximal end and a distal end, the distal end of which is fixed to the second end of the cutting member;

the second access member axially rotatable about the longitudinal axis so that axial rotation of the second access member will move the cutting member between the collapsed first position and the expanded second position;

an expandable tubular tissue removal member having a proximal end, a distal end, an interior surface, an exterior surface, a longitudinal axis, an open, distally located tissue entry opening; a relatively more proximal, tissue exit port, and a tissue removal passageway extending between the proximal and distal ends; and a radio frequency energy source attachable to the cutting member.

65. The radio frequency-assisted tissue removal assembly of claim 64 further comprising a localization wire moveable through the tissue removal passageway.

66. The radio frequency-assisted tissue removal assembly of claim 64 further comprising a tissue collection chamber having a proximal end and a distal end; and where at least one of the distal or proximal ends of the tissue collection chamber additionally defines a port; the port and tissue collection chamber each configured to accommodate the cutting member, first access member, second access member, and a tissue retrieval instrument.

67. The radio frequency-assisted tissue removal assembly of claim 66 further comprising a tissue collection chamber assembly attachable to the tubular tissue removal member proximal end;

the tissue collection chamber assembly having at least one port to accommodate the cutting member, first access member, second access member, and a tissue retrieval instrument;

the tissue collection chamber assembly adapted to at least partially contain the tissue collection chamber.

68. The radio frequency-assisted tissue removal assembly of claim 64 further comprising a trocar moveable through the tissue removal passageway.

69. The radio frequency-assisted tissue removal assembly of claim 64 further comprising a tissue retrieval member moveable through the tissue removal passageway.

70. A tissue removal assembly, comprising:

a cutting member, moveable between a collapsed first position and an expanded second position, the cutting member having a first end, a second end, and at least one cutting surface, the cutting surface capable of mechanically cutting discrete tissue mass;

a first access member having a longitudinal axis, a proximal end and a distal end, the distal end of which is fixed to the first end of the cutting member;

a second access member having a longitudinal axis, a proximal end and a distal end, the distal end of which is fixed to the second end of the cutting member; the second access member axially rotatable about the longitudinal axis so that axial rotation of the second access member will move the cutting member between the collapsed first position and the expanded second position; and an expandable tubular tissue removal member having a proximal end, a distal end, an interior surface, an exterior surface, a longitudinal axis, an open, distally located tissue entry opening; a relatively more proximal, tissue exit port, and a tissue removal passageway extending between the proximal and distal ends.

71. The tissue removal assembly of claim 70 further comprising a localization wire moveable through the tissue removal passageway.

72. The tissue removal assembly of claim 70 further comprising a tissue collection chamber having a proximal end and a distal end; and where at least one of the distal or proximal ends of the tissue collection chamber additionally defines a port; the port and tissue collection chamber each configured to accommodate the cutting member, first access member, second access member, and a tissue retrieval instrument.

73. The tissue removal assembly of claim 72 further comprising a tissue retrieval chamber assembly attachable to the tubular tissue removal member proximal end;

the tissue collection chamber assembly having at least one port to accommodate the cutting member, first access member, second access member, and a tissue retrieval instrument;

the tissue collection chamber assembly adapted to at least partially contain the tissue collection chamber.

74. The tissue removal assembly of claim 70 further comprising a trocar moveable through the tissue removal passageway.

75. The tissue removal assembly of claim 70 further comprising a tissue retrieval member moveable through the tissue removal passageway.

76. A tissue removal assembly, comprising:
a cutting member, moveable between a collapsed first position and an expanded second position, the cutting member having a first end, a second end, and at least one cutting surface;
a first access member having a longitudinal axis, a proximal end and a distal end, the distal end of which is fixed to the first end of the cutting member;
a second access member having a longitudinal axis, a proximal end and a distal end, the distal end of which is fixed to the second end of the cutting member; the second access member axially rotatable about the longitudinal axis so that axial rotation of the second access member will move the cutting member between the collapsed first position and the expanded second position;
an expandable tubular tissue removal member having a proximal end, a distal end, an interior surface, an exterior surface, a longitudinal axis, an open, distally located tissue entry opening; a relatively more proximal, tissue exit port, and a tissue removal passageway extending between the proximal and distal ends; and
where the cutting member is attachable to the distal end of the expandable tubular tissue removal member.

77. The tissue removal assembly of claim 76 further comprising a localization wire moveable through the tissue removal passageway.

78. The tissue removal assembly of claim 76 further comprising a tissue collection chamber having a proximal end and a distal end; and
where at least one of the distal or proximal ends of the tissue collection chamber additionally defines a port; the port and tissue collection chamber each configured to accommodate the cutting member, first access member, second access member, and a tissue retrieval instrument.

79. The tissue removal assembly of claim 78 further comprising a tissue collection chamber assembly attachable to the tubular tissue removal member proximal end;
the tissue collection chamber assembly having at least one port to accommodate the cutting member, first access member, second access member, and a tissue retrieval instrument;
the tissue collection chamber assembly adapted to at least partially contain the tissue collection chamber.

80. The tissue removal assembly of claim 76 further comprising a trocar moveable through the tissue removal passageway.

81. The tissue removal assembly of claim 76 further comprising a tissue retrieval member moveable through the tissue removal passageway.

82. A procedure for removing tissue from a selected internal tissue region, comprising the steps of:
a) introducing, to a position adjacent the selected internal tissue region, a tissue removal member, said member comprising:
a cutting member moveable between a collapsed first position and an expanded second position, the cutting member having a first end, a second end, and at least one cutting surface;
a first access member having a longitudinal axis, a proximal end and a distal end, the distal end of which is fixed to the first end of the cutting member; and
a second access member having a longitudinal axis, a proximal end and a distal end, the distal end of which is fixed to the second end of the cutting member; the second access member axially rotatable about the longitudinal axis so that axial rotation of the second access member will move the cutting member between the collapsed first position and the expanded second position, b) moving and advancing the cutting member to cut a discrete tissue mass in the selected internal tissue region having a diameter generally greater than the tissue removal member, and c) removing the discrete tissue mass through the tissue removal member.

83. The procedure of claim 82 where the cutting member is a radio frequency cutter.

84. The procedure of claim 83 where the radio frequency cutter further comprises a mechanical blade.

85. The procedure of claim 82 where the cutting member is a mechanical blade.

86. The procedure of claim 85 further including the step of vibrating the mechanical blade cutting member.

87. The procedure of claim 85 further including the step of rotating the mechanical blade cutting member.

88. The procedure of claim 82 where the cutting member is an ultrasound cutter.

89. The procedure of claim 82 where the tissue removal member is a braided, expandable tubular member.

90. The procedure of claim 82 further including the step of placing the discrete tissue mass in a tissue collection chamber.

91. The procedure of claim 88 further including the step of delivering the tissue collection chamber containing the discrete tissue mass to a laboratory.

92. The procedure of claim 82 further including the step of further cutting the discrete tissue mass into one or more smaller pieces.

93. A procedure for removing tissue from a selected internal tissue region, comprising the steps of:
a) making an incision in a skin region,
b) introducing to a position adjacent a selected internal tissue region, a trocar, a localization wire, a cutting member moveable between a collapsed first position and an expanded second position, the cutting member having a first end, a second end, and at least one cutting surface, a first access member having a longitudinal axis, a proximal end and a distal end, the distal end of which is fixed to the first end of the cutting member, a second access member having a longitudinal axis, a proximal end and a distal end, the distal end of which is fixed to the second end of the cutting member; the second access member axially rotatable about the longitudinal axis so that axial rotation of the second access member will move the cutting member between the collapsed first position and the expanded second position,
an expandable tissue removal member having an enclosing sheath removably affixed to the exterior surface of the tissue removal member,
c) inserting the localization wire through the selected internal tissue region, d) withdrawing the trocar from the position adjacent the selected internal tissue region, e) removing the enclosing sheath from the tissue removal member, f) moving and advancing the cutting member to cut a discrete tissue mass in the selected internal tissue region having a diameter generally greater than the expandable tissue removal member, and g) removing the discrete tissue mass through the tissue removal member.

94. The procedure of claim 92 where the enclosing sheath is partially removed.

95. The procedure of claim 92 where the enclosing sheath is completely removed.

96. The procedure of claim 92 where the cutting member is a radio frequency cutter.

97. The procedure of claim 95 where the radio frequency cutter further comprises a mechanical blade.

98. The procedure of claim 92 where the cutting member is a mechanical blade.

99. The procedure of claim 97 further including the step of vibrating the mechanical blade cutting member.

100. The procedure of claim 97 further including the step of rotating the mechanical blade cutting member.

101. The procedure of claim 93 where the cutting member is an ultrasound cutter.

102. The procedure of claim 93 where the tissue removal member is a braided, expandable tubular member.

103. The procedure of claim 93 further including the step of placing the discrete tissue mass in a tissue collection chamber.

104. The procedure of claim 103 further including the step of delivering the tissue collection chamber containing the discrete tissue mass to a laboratory for analysis.

105. The procedure of claim 93 further including the step of further cutting the discrete tissue mass into one or more smaller pieces.

106. The tissue removal assembly of claim 51 where the tissue removal member is coated with a coating material.

107. The tissue removal assembly of claim 1 further comprising an extensible tissue separating member attachable to the distal end of the first access member and the distal end of the second access member.

108. The tissue removal assembly of claim 53 where the extensible tissue separating member is serrated.

* * * * *

UNITED STATES PATENT AND TRADEMARK OFFICE
CERTIFICATE OF CORRECTION

PATENT NO. : 6,036,698
DATED : March 14, 2000
INVENTOR(S) : Natalie V. Fawzi, D. Laksen Sirimanne, George D. Hermann, Douglas S. Sutton, and Thomas A. Howell It is certified that error appears in the above-identified patent and that said Letters Patent is hereby corrected as shown below:

Item [56], under "References Cited", please insert the following U.S. Patent Document citations:

| | | |
|---|---|---|
| 1,995,725 | 03/23/31 | Wappler, F.C. |
| 3,174,851 | 03/23/65 | Buehler et al. |
| 3,351,463 | 11/07/67 | Rozner et al. |
| 3,753,700 | 08/21/73 | Harrison et al. |
| 3,989,038 | 11/02/76 | Neward |
| 4,116,198 | 09/26/78 | Roos |
| 4,311,143 | 01/19/82 | Komiya |
| 4,362,160 | 12/07/82 | Hiltebrandt |
| 4,493,320 | 01/15/85 | Treat |
| 4,643,187 | 02/17/87 | Okada |
| 4,657,018 | 04/14/87 | Hakky |
| 4,718,419 | 01/12/88 | Okada |
| 4,811,733 | 03/14/89 | Borsanyi et al. |
| 4,905,691 | 03/06/90 | Rydell |
| 4,921,479 | 05/01/90 | Grayzel |
| 4,944,308 | 07/31/90 | Åkerfeldt |
| 4,953,558 | 09/04/90 | Akerfeldt |
| 5,064,424 | 11/12/91 | Bitrolf |
| 5,078,716 | 01/07/92 | Doll |
| 5,080,660 | 01/14/92 | Buelna |
| 5,085,659 | 02/04/92 | Rydell |
| 5,100,423 | 03/31/92 | Fearnot |
| 5,111,828 | 05/12/92 | Kornberg et al. |
| Re. 34,056 | 09/08/92 | Lindgren et al. |
| 5,158,545 | 10/27/92 | Trudell et al. |
| 5,171,255 | 12/15/92 | Rydell |
| 5,197,484 | 03/30/93 | Kornberg et al. |
| 5,201,756 | 04/13/93 | Horzewski et al. |
| 5,209,749 | 05/11/93 | Buelna |
| 5,217,458 | 06/08/93 | Parins |
| 5,254,105 | 10/19/93 | Haaga |
| 5,312,417 | 05/17/94 | Wilk |
| 5,353,804 | 10/11/94 | Kornberg et al. |
| 5,417,697 | 05/23/95 | Wilk et al. |
| 5,437,665 | 08/01/95 | Munro |

UNITED STATES PATENT AND TRADEMARK OFFICE
CERTIFICATE OF CORRECTION

PATENT NO. : 6,036,698  
DATED : March 14, 2000  
INVENTOR(S) : Natalie V. Fawzi, D. Laksen Sirimanne, George D. Hermann, Douglas S. Sutton, and Thomas A. Howell Page 2 of 3

It is certified that error appears in the above-identified patent and that said Letters Patent is hereby corrected as shown below:

| | | |
|---|---|---|
| 5,480,397 | 01/02/96 | Eggers et al. |
| 5,496,314 | 03/05/96 | Eggers |
| 5,505,728 | 04/09/96 | Ellman et al. |
| 5,526,822 | 06/18/96 | Burbank et al. |
| 5,527,332 | 06/18/96 | Clement |
| 5,569,244 | 10/29/96 | Hahnen |
| 5,578,030 | 11/26/96 | Levin |
| 5,593,406 | 01/14/97 | Eggers et al. |
| 5,611,798 | 03/08/97 | Eggers |
| 5,647,867 | 07/15/97 | Neuberger et al. |
| 5,707,359 | 01/13/98 | Buflini |
| 5,709,697 | 01/20/98 | Ratcliff et al. |
| 5,733,283 | 03/31/98 | Malis et al. |
| 5,741,271 | 04/21/98 | Nakao et al. |
| 5,743,906 | 04/28/98 | Parins et al. |
| 5,759,187 | 06/02/98 | Nakao et al. |
| 5,769,086 | 06/23/98 | Ritchart et al. |
| 5,775,333 | 07/7/98 | Burbank et al. |
| 5,782,775 | 07/21/98 | Milliman et al. |
| 5,795,308 | 08/18/98 | Russin |
| 5,823,971 | 10/20/98 | Robinson et al. |

Column 2,  
Line 11, please delete "this".

Column 9,  
Line 27, replace "(212)" with -- (210) --.

Column 11,  
Line 47, replace "the removal assembly" with -- the tissue removal assembly --.

Column 17,  
Line 40, replace "loaded with -- limited --.  
Line 42, replace "patent" with -- patent --.

Column 24, claim 91,  
Replace "claim 88" with -- claim 90 --.

Column 25. claim 94,  
Replace "claim 92" with -- claim 93 --.

UNITED STATES PATENT AND TRADEMARK OFFICE
CERTIFICATE OF CORRECTION

PATENT NO.   : 6,036,698
DATED        : March 14, 2000
INVENTOR(S)  : Natalie V. Fawzi, D. Laksen Sirimanne, George D. Hermann, Douglas S. Sutton, and Thomas A. Howell It is certified that error appears in the above-identified patent and that said Letters Patent is hereby corrected as shown below:

Column 25. claim 95,
Replace "claim 92" with -- claim 93 --.

Column 25. claim 96,
Replace "claim 92" with -- claim 93 --.

Column 25, claim 97,
Replace "claim 95" with -- claim 96 --.

Column 25. claim 98,
Replace "claim 92" with -- claim 93 --.

Column 25. claim 99,
Replace "claim 97" with -- claim 98 --.

Column 25. claim 100,
Replace "claim 97" with -- claim 98 --.

Signed and Sealed this

Eighth Day of January, 2002

Attest:

JAMES E. ROGAN
*Director of the United States Patent and Trademark Office*

*Attesting Officer*